(12) United States Patent
Hammami et al.

(10) Patent No.: US 7,851,091 B2
(45) Date of Patent: Dec. 14, 2010

(54) COMPOSITIONS, REDOX COUPLES AND USES THEREOF

(75) Inventors: Amer Hammami, Ville Mont-Royal (CA); Benoît Marsan, Sainte-Julie (CA)

(73) Assignee: Transfert Plus, S.E.C., West Montreal, Quebec (CA)

( * ) Notice: Subject to any disclaimer, the term of this patent is extended or adjusted under 35 U.S.C. 154(b) by 1175 days.

(21) Appl. No.: 11/299,967

(22) Filed: Dec. 13, 2005

(65) Prior Publication Data

US 2006/0127775 A1   Jun. 15, 2006

Related U.S. Application Data

(60) Provisional application No. 60/635,015, filed on Dec. 13, 2004.

(51) Int. Cl.
*H01M 6/16* (2006.01)
(52) U.S. Cl. .................. 429/324; 546/22; 548/112; 564/12; 564/15
(58) Field of Classification Search .......... None
See application file for complete search history.

(56) References Cited

U.S. PATENT DOCUMENTS

| | | | |
|---|---|---|---|
| 5,283,310 A | 2/1994 | Armand et al. | |
| 6,120,696 A | 9/2000 | Armand et al. | |
| 6,319,428 B1 | 11/2001 | Michot et al. | |
| 6,682,855 B2 | 1/2004 | Michot et al. | |

OTHER PUBLICATIONS

Stathatos et al., Chem. Mater., vol. 15, pp. 1825-1829, 2003.
Nusbaumer et al., Chem. Eur. J., vol. 9, pp. 3756-3763, 2003.
Skotheim et al., J. Electrochem. Soc., vol. 132, No. 9, pp. 2116-2120, 1985.
Vijh et al., Bull. Electrochem., vol. 5, No. 6, pp. 456-461, 1989.
Philias et al., Electrochimica Acta, vol. 44, pp. 2915-2926, 1999.
Smith et al., J. Org. Chem., vol. 65, No. 26, pp. 8831-8838, 2000.
Collinson et al., Chem. Soc. Rev., vol. 31, pp. 147-156, 2002.
Maeda, H. et al., One-Step Transformation of Carboxylic Acids into Aldehydes Induced by the Electrochemical Oxidation of Ph3P, Chem. Pharm. Bull., vol. 42, No. 5, May 1994, pp. 1041-1044.
Every, H. A. et al., Substituted Imidazoles as Proton Transport Facilitators in Fuel Cell Membranes, Joint International Meeting—206th Meeting of the Electrochemical Society, 2004 Fall Meeting of the Electrochemical Society of Japan—Meeting Abstracts 2004, p. 1969.
Lide, D. R., Dissociation Constants of Organic Acids and Bases, CRC Handbook on Physics and Chemistry, 86th Edition, 2005-2006, pp. 8-42-8-51.
Olah, G. A., Organophosphorus Compounds. XI. 1H and 31P Nuclear Magnetic Resonance Study of the Protonation of Phosphines, Journal of Organic Chemistry, vol. 34, No. 6, Jun. 1969, pp. 1832-1834.

Zhang, X.-M., Equilibrium Acidities and Homolytic Bond Dissociation Energies of the Acidic C-H Bonds in P-Substituted Triphenylphosphonium Cations, Journal Am. Chem. Soc., vol. 116, No. 3, 1994, pp. 968-972.
Ge, Y. et al., Electrochemically Controlled Hydrogen Bonding. o-Quinones as Simple Redox-Dependent Receptors for Arylureas, Journal of Organic Chemistry, vol. 65, No. 26, Dec. 29, 2000, pp. 8831-8838.

(Continued)

*Primary Examiner*—Daniel M Sullivan
*Assistant Examiner*—Chukwuma O Nwaonicha
(74) *Attorney, Agent, or Firm*—Bereskin & Parr LLP/S.E.N.C.R.L., s.r.l.

(57) ABSTRACT

There are provided compositions comprising a first compound selected from the group consisting of compounds of formulas (Ib), (III), (V), and (VII), and a second compound selected from the group consisting of compounds of formulas (IIb), (IV), (VI), and (VIII):

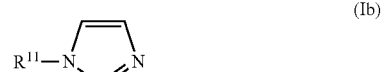

(Ib)

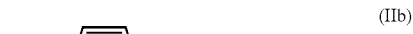

(IIb)

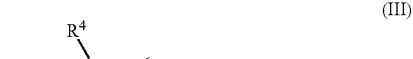

(III)

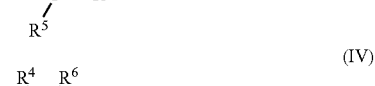

(IV)

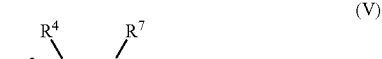

(V)

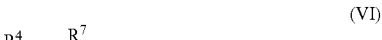

(VI)

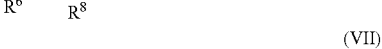

(VII)

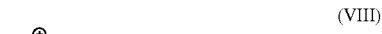

(VIII)

Various chemical entities can be used for $R^4$ to $R^{11}$. These compositions can be particularly useful as anti-static agents or as electron activable precursors to a redox couple.

41 Claims, 3 Drawing Sheets

OTHER PUBLICATIONS

Tucker, J. H. R. et al., Recent Developments in the Redox-Switched Binding of Organic Compounds, Chem. Soc. Rev., vol. 31, Mar. 18, 2002, pp. 147-156.

Lund, H. et al., Organic Electrochemistry, 4th Edition, 2001, Marcel Dekker, Inc., Chapters 15, 17, 18, 20.

Kargin, Y. M., et al., Electrochemistry of Organophosphorus Compounds, Russian Journal of General Chemistry, vol. 71, No. 9, 2001, pp. 1393-1421.

Hagiwara, R. et al., A Highly Conductive Room Temerature Molten Fluoride: EMIF-2.3HF, Journal of The Electrochemical Society, 149 (1) D1-D6 (2002), Kyoto, Japan.

COMPOSITIONS, REDOX COUPLES AND USES THEREOF

CROSS-REFERENCE TO RELATED APPLICATION

The present application claims priority on U.S. provisional application No. 60/635,015 filed on Dec. 13, 2004, which is incorporated herein by reference in its entirety.

TECHNICAL FIELD

The present invention relates to improvements in the field of electrochemistry. In particular, this invention relates to compositions that can be used for various purposes such as anti-static agents or for preparing redox couples or reversible switchable systems.

BACKGROUND OF THE INVENTION

Sun is a free and unlimited renewable source of energy. It can be converted directly to electricity by using p-n heterojunction solar cells (like silicon-based devices), electrochemical photovoltaic cells (EPC's) or dye-sensitized solar cells (DSSC's). EPC's are systems based on a junction between a semiconductor (p-type or n-type) and an electrolyte containing one redox couple; an auxiliary electrode completes the device. Owing to the built-in potential developed at the semiconductor/electrolyte interface, the photogenerated electrons and holes are separated and used to undergo oxidation and reduction reactions at the electrodes, respectively with the reduced and oxidized species of the redox couple. On the other hand, DSSC's are systems based on a junction between dye-chemisorbed nanocristalline $TiO_2$ particles, deposited on a conductive glass substrate, and a non-aqueous electrolyte containing the $I^-/I_3^-$ redox couple; a platinum-coated conductive glass electrode completes the device. In such systems, the light absorption (by the dye molecules) and charge-carrier transport (in the conduction band of the semiconductor to the charge collector) processes are separated. Homogeneous oxidation of $I^-$ species serves to regenerate the photoexcited dye molecules whereas the heterogeneous reduction of $I_3^-$ species takes place at the platinum-coated electrode.

There is extensive prior art on EPC's and DSSC's. However, one main issue still to resolve is to find a redox couple that is electrochemically stable, non-corrosive, with a high degree of reversibility and a high electropositive (in conjunction with n-type semiconductors) or electronegative (in conjunction with p-type semiconductors) potential, and colorless when used in concentrations allowing high electrolyte ionic conductivities.

$I^-/I_3^-$ is the most investigated redox couple for DSSC's. Cations may be alkali metals or organic cations containing quaternary ammonium groups such as dialkylimidazolium (Stathatos et al., Chem. Mater., 15, 1825 (2003)). The main limitations of this system are (i) the fact that it absorbs a significant part of the visible light of the solar spectrum when used in the concentration range giving reasonably good ionic conductivities (which leads to a decrease in the energy conversion efficiency); (ii) its too low redox potential (which limits the device photovoltage); (iii) its reactivity towards silver (which prevents the use of this metal as a current collector); and (iv) the high volatility of the electrolyte when usual organic solvents are employed (which causes an irreversible instability of the device).

Nusbaumer et al. in Chem. Eur. J., 9, 3756 (2003) studied alternative redox couples for DSSC's based on much more expensive cobalt complexes. Although the fact that these systems are less colored and possess more positive potential than the $I^-/I_3^-$ redox couple, the oxidized species ($Co^{III}$) may be reduced at the conductive glass acting as a substrate for the $TiO_2$ particles, in which case the energy conversion efficiency is decreased. Moreover, regeneration of the dye molecules by the reduced species ($Co^{II}$) (absolutely necessary to the operation of the device) may become more difficult due to association of the oxidized species ($Co^{III}$) with the sensitizer.

In EPC's, various redox couples dissolved in water were studied, such as $Fe(CN)_6^{4-}/Fe(CN)_6^{3-}$, $I^-/I_3^-$ $Fe^{2+}/Fe^{3+}$, $S^{2-}/S_n^{2-}$, $Se^{2-}/Se_n^{2-}$ and $V^{2+}/V^{3+}$, and devices exhibiting a good energy conversion efficiency were generally unstable under sustained white light illumination due to photocorrosion of the semiconductor electrode. The use of non-aqueous electrolytic media (liquid, gel or polymer) could eliminate the photocorrosion process, but in these cases the number of redox couples is very limited. For examples, the $I^-/I_3^-$ (Skotheim and Inganäs, J. Electrochem. Soc., 132, 2116 (1985)) and $S^{2-}/S_n^{2-}$ (Vijh and Marsan, Bull. Electrochem., 5, 456 (1989)) redox couples were dissolved in polyethylene oxide (PEO) and modified PEO, respectively, and investigated in EPC's. In addition to the coloration and potential problems occurring with the $I^-/I_3^-$ couple, as mentioned above, the device stability has not been demonstrated. Regarding the $S^{2-}/S_n^{2-}$ redox couple, the same problems were observed but in this case the stability under white light illumination has been reported.

A cesium thiolate (CsT)/disulfide ($T_2$) redox couple, where $T^-$ stands for 5-mercapto-1-methyltetrazolate ion and $T_2$ for the corresponding disulfide, was dissolved in modified PEO and studied in an EPC (Philias and Marsan, Electrochim. Acta, 44, 2915 (1999)). Its more positive potential than that of the $S^{2-}/S_n^{2-}$ redox couple, its better dissociation in organic media including polymers (giving much more conductive electrolytes) and its much less intense coloration are responsible for the significant increase of the device energy conversion efficiency. Despite this improvement, the $T^-/T_2$ redox couple is quite electrochemically irreversible, with a difference between the anodic ($E_{pa}$) and cathodic ($E_{pc}$) peak potentials, symbolized as $\Delta E_p$, of 1.70 V at a platinum electrode (scanning speed of 100 mV/s), even when put in a more conductive gel electrolyte comprising 50 mM of $T^-$ and 5 mM of $T_2$ dissolved in 80% DMF/DMSO (60/40) and incorporated in 20% poly(vinylidene fluoride), PVdF. Furthermore, its solubility is not very good in organic media.

Smith et al. in J. Org. Chem., 65, 8831 (2000) studied the redox hydrogen-bonded system formed from host-guest interactions with organic molecules that can bind through hydrogen bond and found that the redox couple of phenanthrenequinone (host) and urea (guest) undergoes a reversible one-electron reduction in aprotic medium. Collinson et al. gave more details about different kinds of redox-switched binding compounds (Collinson et al., Chem., soc., Rev. 31, 147-156, 2002). The articles of Smith et al. and Collinson et al. are hereby incorporated by reference.

Thus, based on prior art relative to redox couples for EPC's and DSSC'S, there are no redox couples permitting to considerably optimize the device energy conversion efficiency.

Therefore, new redox couples having improved properties with respect to the redox couples of the prior art would be highly desired. Moreover, redox couples permitting to avoid the drawbacks of the prior art are also highly desired. Finally, compositions or precursors that permit to easily prepare such redox couples would also highly be desired.

SUMMARY OF THE INVENTION

According to one aspect of the invention, there is provided a composition comprising a first compound selected from the group consisting of compounds of formulas (I), (III), (V), and (VII), and a second compound selected from the group consisting of compounds of formulas (II), (IV), (VI), and (VIII):

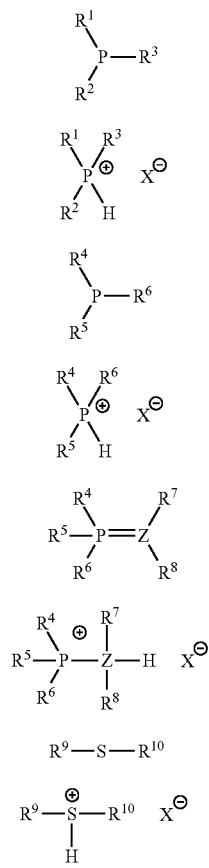

wherein $R^1$, $R^2$ and $R^3$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^1$ and $R^2$ are joined together to form a 5 to 14 membered heterocyclyl in which $R^3$ is absent, a hydrogen atom, or a bond between N and $R^1$ or between N and $R^2$; or to form a 5 to 14 membered heteroaryl in which $R^3$ is absent, a hydrogen atom, a bond between N and $R^1$ or between N and $R^2$, or is a part of polymer chain or network;

$R^4$, $R^5$ and $R^6$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, $(CH_3)_2N-$, $(C_2H_5)_2N-$, $(C_3H_7)_2N-$, $(C_4H_9)_2N-$, $(i-Pr)_2N-$, $C_nH_{2n+1}$, $Ph_2P(O)-$, $Ph_2P-$, $Me_2P(O)-$, $Me_2P$, $Ph_2P(S)$, $Me_2P(S)$, $Ph_3P=N-$, $Me_3P=N-$, and part of polymer chain or network, or $R^4$ and $R^5$ are joined together to form a 5 to 14 membered heterocyclyl in which $R^6$ is absent, a hydrogen atom, or a bond between P and $R^4$ or between P and $R^5$; or to form a 5 to 14 membered heteroaryl ring in which $R^6$ is absent, a hydrogen atom, a bond between P and $R^4$ or between P and $R^5$, or is a part of polymer chain or network;

$R^7$ and $R^8$ are the same or different and are selected from the group consisting of H, $CF_3$, $C_nF_{2n+1}$, $SO_2H-$, $-SO_2CF_3$, $-NSO_2CF_3-$, $-SO_2CH_3$, $-NSO_2CH_3$, $C_1$-$C_{12}$ alkyl which is linear or branched, $C_6$-$C_{12}$ aryl, $C_nH_{2n+1}$, CN, $NO_2$, $Ph_2P(O)-$, $Ph_2P-$, $Me_2P(O)-$, $Me_2P$, $Ph_2P(S)$, $Me_2P(S)$, $Ph_3P=N-$, $Me_3P=N-$, $C_6H_5C_pH_{2p}-$, $C_pH_{2p+1}C_6H_4-$, $C_pH_{2p+1}C_6H_4C_nH_{2n}-$, $CH_2=CHC_pH_{2p}-$, $CH_2=CHC_6H_5-$, $CH_2=CHC_6H_4C_pH_{2p+1}-$, $CH_2=CHC_pH_{2p}C_6H_4-$,

and part of polymer chain or network;

$R^9$ and $R^{10}$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^9$ and $R^{10}$ are joined together to form a 5 to 7 membered heterocyclyl or heteroaryl; and $X^-$ is $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, $2.3HF$, $Cl^-$, $Br^-$, $I^-$, $PF_6^-$, $BF_4^-$, $ClO_4^-$, saccharin(o-benzoic sulfimide), $(C_8H_{16}SO_2)_2N^-$, or $C_3H_3N_2^-$;

Z is C, N or As;

the alkyl, cycloalkyl, heterocyclyl, alkenyl, alkynyl, aryl, aralkyl, alkylaryl, and heteroaryl being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $CF_3$, $SO_3^-$, $C_nF_{2n+1}$, $C_1$-$C_{12}$ alkyl which is linear or branched, $C_6$-$C_{12}$ aryl, $C_nH_{2n+1}$, $Ph_2P(O)-$, $Ph_2P-$, $Me_2P(O)-$, $Me_2P$, $Ph_2P(S)$, $Me_2P(S)$, $Ph_3P=N-$, $Me_3P=N-$, $C_6H_5C_pH_{2p}-$, $C_pH_{2p+1}C_6H_4-$, $C_pH_{2p+1}C_6H_4C_nH_{2n}-$, $CH_2=CHC_pH_{2p}-$, $CH_2=CHC_6H_5-$, $CH_2=CHC_6H_4C_pH_{2p+1}-$, and $CH_2=CHC_pH_{2p}C_6H_4-$, where n is an integer having a value from 1 to 48 (preferably 1 to 12) and p is an integer having a value from 1 to 48 (preferably 1 to 12).

According to another aspect of the present invention, there is provided a composition comprising a compound of formula (I) and a compound of formula (II); a compound of formula (III) and a compound of formula (IV); a compound of formula (V) and a compound of formula (VI); or a compound of formula (VII) and a compound of formula (VIII), the compounds of formulas (I), (II), (III), (IV), (V), (VI), (VII) or (VIII) being as previously defined.

It was found that the compositions of the present invention can be useful as precursors to redox couples. In fact, it was shown that such compositions can be easily activated so as to be converted into a redox couple. These compositions are simple, easy to prepare and to convert into redox couples. It was also found that such compositions can be used to efficiently prepare redox couples without involving tedious tasks. Moreover, it has been found that these compositions have a good thermal stability, a good solubility in various solvents. It also has been found that these compositions are substantially colorless at concentrations permitting a good conductivity. Finally, it was found that such compositions can be used as anti-static agents or in the manufacture of articles having anti-static properties.

According to another aspect of the invention, there is provided a kit for preparing a redox couple, the kit comprising a composition according to the present invention, together with instructions indicating how to convert at least a part of the composition into a redox couple.

According to another aspect of the invention, there is provided a kit for preparing a redox couple, the kit comprising:
a compound of formula (I), (III), (V), or (VII);
instructions indicating how to convert at least a part of the compound of formula (I), (III), (V), or (VII) into its conjugated acid of formula (II), (IV), (VI), or (VII), respectively, so as to obtain a composition comprising a compound of formula (I) and a compound of formula (II); a compound of formula (III) and a compound of formula (IV); a compound of formula (V) and a compound of formula (VI); or a compound of formula (VII) and a compound of formula (VIII); and
instructions indicating how to convert at least a part of the composition into a redox couple,
wherein the compounds of formulas (I), (II), (III), (IV) (V), (VI), (VII) or (VIII) are as previously defined. Such a kit preferably further comprises a proton source such as a compound of formula HX, where X is as previously defined. Alternatively, the kit can also comprise another type of proton source such as a catalyst, or a proton exchange resin so as to convert the compound of formula (I), (III), (V), or (VII).

According to another aspect of the invention, there is provided a kit comprising:
a first compound selected from the group consisting of compounds of formulas (I), (III), (V), and (VII), and a second compound selected from the group consisting of compounds of formulas (II), (IV), (VI), and (VIII); and
instructions indicating how to prepare a redox couple from the compounds,
wherein the compounds of formulas (I), (II), (III), (IV), (V), (VI), (VII) or (VIII) are as previously defined. Such a kit preferably comprises a compound of formula (I) and a compound of formula (II); a compound of formula (III) and a compound of formula (IV); a compound of formula (V) and a compound of formula (VI); or a compound of formula (VII) and a compound of formula (VIII).

It was found that the kits of the present invention can be useful for expediently prepare redox couples. In fact, these kits can be used to simply, rapidly and at low costs prepare redox couples. By using, these kits, redox couples can be prepared without having recourse to tedious or complicated tasks.

According to another aspect of the invention, there is provided a process for preparing a redox couple comprising the step of activating a composition as defined in the present invention so as to convert at least a part of the composition into the redox couple. The activating step can be carried out by withdrawing at least one electron to a compound of the composition. The activating step is preferably carried out by means of an electron source. The composition can be prepared by reacting a selected amount of the first compound of formula (I), (III), (V), or (VII) with a proton source so as to obtain the second compound and then mixing together another selected amount of the first compound with the second compound so as to obtain the composition. Alternatively, a proton source, in an equimolar ratio less than 1, can be added to the first compound (i.e. if as example 1 mole of the first compound is used, less than 1 mole of proton will be used) so that such an addition of proton to the first compound permits to obtain the composition comprising the first and second compounds.

It was found that such a process can be very efficient in the preparation of a redox couple. Such a process implies only simple reagents and can be easily and rapidly carried out.

According to another aspect of the invention, there is provided a redox couple according to any one of schemes 1 to 4:

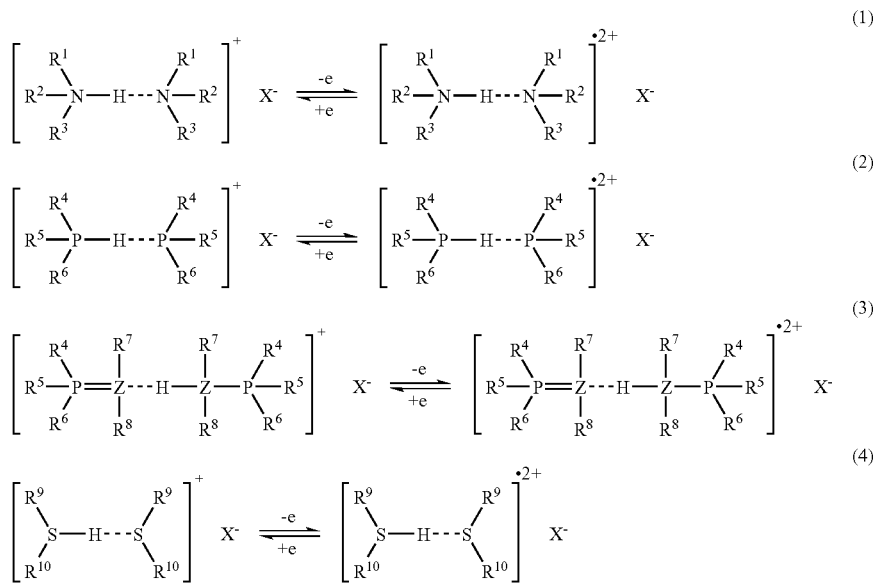

wherein $R^1$, $R^2$ and $R^3$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^1$ and $R^2$ are joined together to form a 5 to 14 membered heterocyclyl in which $R^3$ is absent, a hydrogen atom, or a bond between N and $R^1$ or between N and $R^2$; or to form a 5 to 14 membered heteroaryl in which $R^3$ is absent, a hydrogen atom, a bond between N and $R^1$ or between N and $R^2$, or is a part of polymer chain or network;

$R^4$, $R^5$ and $R^6$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, $(CH_3)_2N$—, $(C_2H_5)_2N$—, $(C_3H_7)_2N$—, $(C_4H_9)_2N$—, $(i\text{-}Pr)_2N$—, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, and part of polymer chain or network, or $R^4$ and $R^5$ are joined together to form a 5 to 14 membered heterocyclyl in which $R^6$ is absent, a hydrogen atom, or a bond between P and $R^4$ or between P and $R^5$; or to form a 5 to 14 membered heteroaryl ring in which $R^6$ is a absent, a hydrogen atom, a bond between P and $R^4$ or between P and $R^5$, or is a part of polymer chain or network;

$R^7$ and $R^8$ are the same or different and are selected from the group consisting of H, $CF_3$, $C_nF_{2n+1}$, $SO_2H$—, —$SO_2CF_3$, —$NSO_2CF_3$—, —$SO_2CH_3$, —$NSO_2CH_3$, $C_1$-$C_{12}$ alkyl which is linear or branched, $C_6$-$C_{12}$ aryl, $C_nH_{2n+1}$, CN, $NO_2$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4$—, $C_pH_{2+1}C_6H_4C_nH_{2n}$—, $CH_2=CHC_pH_{2p}$—, $CH_2=CHC_6H_5$—, $CH_2=CHC_6H_4C_pH_{2p+1}$—, $CH_2=CHC_pH_{2p}C_6H_4$—,

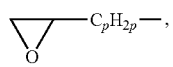

and a part of polymer chain or network;

$R^9$ and $R^{10}$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and a part of polymer chain or network, or $R^9$ and $R^{10}$ are joined together to form a 5 to 7 membered heterocyclyl or heteroaryl; and $X^-$ is $(FSO_2)_2N^-$, $(CF_3SO_2)_2N^-$, $(C_2F_5SO_2)_2N$—, $(CF_3SO_2)_3C^-$, $CF_3SO_3^-$, $CF_3COO^-$, $AsF_6^-$, $CH_3COO^-$, $(CN)_2N^-$, $NO_3^-$, $2.3HF$, $Cl^-$, $Br^-$, $I^-$, $PF_6^-$, $BF_4^-$, $ClO_4^-$, saccharin(o-benzoic sulfimide), $(C_8H_{16}SO_2)_2N^-$, or $C_3H_3N_2^-$;

Z is C, N or As;

the alkyl, cycloalkyl, heterocyclyl, alkenyl, alkynyl, aryl, aralkyl, alkylaryl, and heteroaryl being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $CF_3$, $SO_3^-$, $C_nF_{2n+1}$, $C_1$-$C_{12}$ alkyl which is linear or branched, $C_6$-$C_{12}$ aryl, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHC_6H_4C_pH_{2p+1}$—, and $CH_2=CHC_pH_{2p}C_6H_4$—.

where n is an integer having a value from 1 to 48 (preferably 1 to 12) and p is an integer having a value from 1 to 48 (preferably 1 to 12).

It was found that the redox couples of the present invention can have a high reversibility since they have a very small $\Delta E_p$. Moreover, it has been found that these redox couples have a good thermal stability, a good solubility in various solvents and an excellent ionic conductivity in a non-aqueous medium. It also has been found that these redox couples are substantially colorless at concentrations permitting a good conductivity. Such characteristics make them particularly interesting in various applications like solar cells or photovoltaic cells. It also has been found that some members of these couples are highly electropositive and some others are highly electronegative. It also has been found that these redox couples do not have tendency to corrode other components when used in devices such as solar cells or photovoltaic cells.

According to another aspect of the invention, there is provided a redox-switchable system according to any one of schemes 10 to 13:

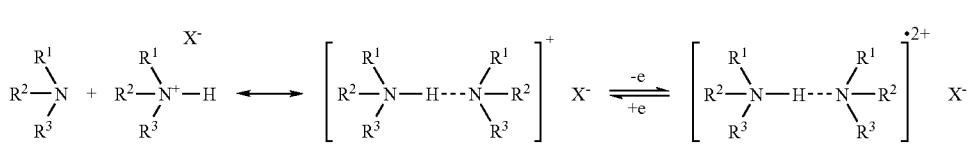

(10)

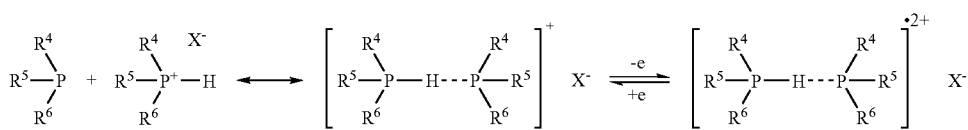

(11)

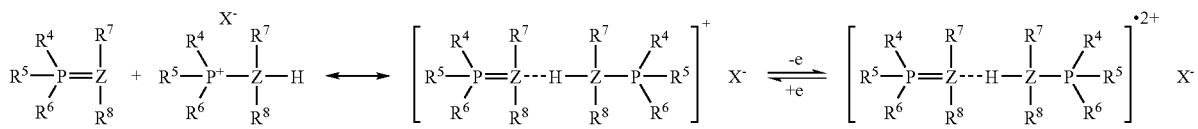

(12)

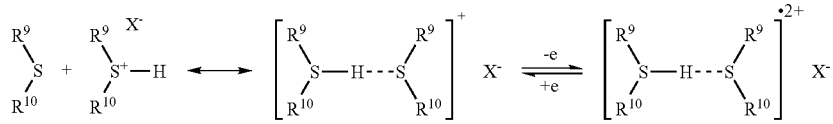
(13)

wherein

R$^1$, R$^2$ and R$^3$ are the same or different and are selected from the group consisting of a hydrogen atom, C$_1$-C$_{12}$ alkyl which is linear or branched, C$_3$-C$_{12}$ cycloalkyl, C$_1$-C$_{12}$ heterocyclyl, C$_2$-C$_8$ alkenyl, C$_2$-C$_8$ alkynyl, C$_6$-C$_{12}$ aryl, C$_6$-C$_{20}$ aralkyl, C$_6$-C$_{20}$ alkylaryl, C$_1$-C$_{12}$ heteroaryl, and part of polymer chain or network, or R$^1$ and R$^2$ are joined together to form a 5 to 14 membered heterocyclyl in which R$^3$ is absent, a hydrogen atom, or a bond between N and R$^1$ or between N and R$^2$; or to form a 5 to 14 membered heteroaryl in which R$^3$ is absent, a hydrogen atom, a bond between N and R$^1$ or between N and R$^2$, or is a part of polymer chain or network;

R$^4$, R$^5$ and R$^6$ are the same or different and are selected from the group consisting of a hydrogen atom, C$_1$-C$_{12}$ alkyl which is linear or branched, C$_3$-C$_{12}$ cycloalkyl, C$_1$-C$_{12}$ heterocyclyl, C$_2$-C$_8$ alkenyl, C$_2$-C$_8$ alkynyl, C$_6$-C$_{12}$ aryl, C$_6$-C$_{20}$ aralkyl, C$_6$-C$_{20}$ alkylaryl, C$_1$-C$_{12}$ heteroaryl, (CH$_3$)$_2$N—, (C$_2$H$_5$)$_2$N—, (C$_3$H$_7$)$_2$N—, (C$_4$H$_9$)$_2$N—, (i-Pr)$_2$N—, C$_n$H$_{2n+1}$, Ph$_2$P(O)—, Ph$_2$P—, Me$_2$P(O)—, Me$_2$P, Ph$_2$P(S), Me$_2$P(S), Ph$_3$P=N—, Me$_3$P=N—, and part of polymer chain or network, or R$^4$ and R$^5$ are joined together to form a 5 to 14 membered heterocyclyl in which R$^6$ is absent, a hydrogen atom, or a bond between P and R$^4$ or between P and R$^5$; or to form a 5 to 14 membered heteroaryl ring in which R$^6$ is absent, a hydrogen atom, a bond between P and R$^4$ or between P and R$^5$, or is a part of polymer chain or network;

R$^7$ and R$^8$ are the same or different and are selected from the group consisting of H, CF$_3$, C$_n$F$_{2n+1}$, —SO$_2$H, —SO$_2$CF$_3$, —NSO$_2$CF$_3$, —SO$_2$CH$_3$, —NSO$_2$CH$_3$, C$_1$-C$_{12}$ alkyl which is linear or branched, C$_6$-C$_{12}$ aryl, C$_n$H$_{2n+1}$, CN, NO$_2$, Ph$_2$P(O)—, Ph$_2$P—, Me$_2$P(O)—, Me$_2$P, Ph$_2$P(S), Me$_2$P(S), Ph$_3$P=N—, Me$_3$P=N—, C$_6$H$_5$C$_p$H$_{2p}$—, C$_p$H$_{2p+1}$C$_6$H$_4$—, C$_p$H$_{2p+1}$C$_6$H$_4$C$_n$H$_{2n}$—, CH$_2$=CHC$_p$H$_{2p}$—, CH$_2$=CHC$_6$H$_5$—, CH$_2$=CHC$_6$H$_4$C$_p$H$_{2p+1}$—, CH$_2$=CHC$_p$H$_{2p}$C$_6$H$_4$—,

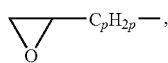

and part of polymer chain or network,

R$^9$ and R$^{10}$ are the same or different and are selected from the group consisting of a hydrogen atom, C$_1$-C$_{12}$ alkyl which is linear or branched, C$_3$-C$_{12}$ cycloalkyl, C$_1$-C$_{12}$ heterocyclyl, C$_2$-C$_8$ alkenyl, C$_2$-C$_8$ alkynyl, C$_6$-C$_{12}$ aryl, C$_6$-C$_{20}$ aralkyl, C$_6$-C$_{20}$ alkylaryl, C$_1$-C$_{12}$ heteroaryl, and part of polymer chain or network, or R$^9$ and R$^{10}$ are joined together to form a 5 to 7 membered heterocyclyl or heteroaryl; and X is (FSO$_2$)$_2$N$^-$, (CF$_3$SO$_2$)$_2$N$^-$, (C$_2$F$_5$SO$_2$)$_2$N$^-$, (CF$_3$SO$_2$)$_3$C$^-$, CF$_3$SO$_3^-$, CF$_3$COO$^-$, AsF$_6^-$, CH$_3$COO$^-$, (CN)$_2$N$^-$, NO$_3^-$, 2.3HF, Cl$^-$, Br$^-$, I$^-$, PF$_6^-$, BF$_4^-$, ClO$_4^-$, saccharin(o-benzoic sulfimide), (C$_8$H$_{16}$SO$_2$)$_2$N$^-$, or C$_3$H$_3$N$_2^-$;

Z is C, N or As;

the alkyl, cycloalkyl, heterocyclyl, alkenyl, alkynyl, aryl, aralkyl, alkylaryl, and heteroaryl being unsubstituted or substituted with 1 to 3 substituents selected from the group consisting of F, Cl, Br, I, OH, a C$_1$-C$_6$ alkoxy, a C$_1$-C$_6$ hydroxy alkyl, NO$_2$, CN, CF$_3$, SO$_3^-$, C$_n$F$_{2n+1}$, C$_1$-C$_{12}$ alkyl which is linear or branched, C$_6$-C$_{12}$ aryl, C$_n$H$_{2n+1}$, Ph$_2$P(O)—, Ph$_2$P—, Me$_2$P(O)—, Me$_2$P, Ph$_2$P(S), Me$_2$P(S), Ph$_3$P=N—, Me$_3$P=N—, C$_6$H$_5$C$_p$H$_{2p}$—, C$_p$H$_{2p+1}$C$_6$H$_4$—, C$_p$H$_{2p+1}$C$_6$H$_4$C$_n$H$_{2n}$—, CH$_2$=CHC$_p$H$_{2p}$—, CH$_2$=CHC$_6$H$_5$—, CH$_2$=CHC$_6$H$_4$C$_p$H$_{2p+1}$—, and CH$_2$=CHC$_p$H$_{2p}$C$_6$H$_4$—.

where n is an integer having a value from 1 to 48 (preferably 1 to 12) and p is an integer having a value from 1 to 48 (preferably 1 to 12).

The expression "electron activation" is used herein as a synonym of "electron transfer".

The expression "part of polymer chain or network" as used herein when referring to a particular group, such as a R group, means that such a R group is part of a polymer matrix, chain or resin or that such a R group is linked to a polymer matrix, chain or resin.

The term "aryl" as used herein refers to a cyclic or polycyclic aromatic ring. Preferably, the aryl group is phenyl or napthyl.

The term "heteroaryl" as used herein refers to an aromatic cyclic or fused polycyclic ring system having at least one heteroatom selected from the group consisting of N, O, and S. Preferred heteroaryl groups are furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The term "heterocyclyl" includes non-aromatic rings or ring systems that contain at least one ring having at least one hetero atom (such as nitrogen, oxygen or sulfur). Preferably, this term includes all of the fully saturated and partially unsaturated derivatives of the above mentioned heteroaryl groups. Examples of heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl.

The compositions of the present invention can be suitable as electron activable precursors for various redox couples. These compositions, upon electron activation, can be suitable for acting as redox couples. Alternatively, upon electron activation, these compositions can be at least partially converted into redox couples. Preferably, the electron activation is carried out by withdrawing at least one electron to a compound of composition. The compositions of the invention can be effective as precursors to a redox couples, the precursors being electron activable in order to be converted into the redox couples. The compositions of the present invention preferably comprise a compound of formula (I) and a compound of formula (II); a compound of formula (III) and a compound of formula (IV); a compound of formula (V) and a compound of formula (VI); or a compound of formula (VII) and a compound of formula (VIII).

In the compositions of the present invention, the first compound can be present in a molar ratio of about 0.1 to about 99.9% and the second compound can be present in a molar ratio of about 99.9 to about 0.1%. The first compound is preferably present in the composition in a molar ratio of about 10.0 to about 90.0% and the second compound is preferably present in a molar ratio of about 90.0 to about 10.0%.

The compositions, upon electron activation, can have a conductivity of at least $10^{-7}$ S/cm (preferably at least $10^{-6}$ S/cm, more preferably at least $10^{-4}$ S/cm) at 250° C. at a 1 mM concentration for each of the first and second compounds. Alternatively, the conductivity can be of about $10^{-7}$ S/cm to about 1 S/cm at 25° C. and at a 1 mM concentration for each of the first and second compounds.

The unactivated compositions (without any electron activation) can have a conductivity of at least $10^{-12}$ S/cm (preferably at least $10^{-7}$ S/cm, more preferably at least $10^{-6}$ S/cm) at 25° C. at a concentration of about 1 mM to 100 mM for each of the first and second compounds. Alternatively, the conductivity can be of about $10^{-12}$ S/cm to about $10^{-6}$ S/cm at 25° C. and at a 1 mM concentration for each of the first and second compounds.

The compositions of the present invention can be in a solid form and/or in a liquid form at room temperature. The compositions can be used as precursors to redox couples or as anti-static agents. They can also be used for preparing corresponding redox couples or in the manufacture of redox couples, wherein the compositions are electron activated in order to obtain the redox couples. Alternatively, they can be used in the manufacture of articles having anti-static properties. Such articles can be papers, textiles, polymers, clothes, inks, waxes, cleaning compositions, softening compositions or agents, petroleum-based compositions, compositions comprising volatile or flammable ingredients, molded objects, shaped articles, various articles comprising a polymer, a part of an electronic device (such as a computer, TV, DVD, CD player, etc.)

The compositions of the present invention can also be used as non-aqueous proton donor-acceptors to support ionic conduction in proton conducting membranes. They can also be used as proton donor-acceptors to support ionic conduction in proton conducting membranes or as anti-static agents effective in a non-polar medium. The non-polar medium can be petroleum or a derivative thereof, a polymer (such as polyurethanes, polyvinyl chlorides, polystyrenes, polyesters, polyethylenes, polypropylenes, or polyethylenetherephtalates), a textile or an ink. The non-polar medium can also be a non-polar solvent such as hydrocarbons and particularly alkanes, preferably $C_5$-$C_{15}$ alkanes.

In the compositions, kits, and redox-switchable systems of the present invention comprising a compound of formula (I), preferably no more than one of $R^1$, $R^2$ and $R^3$ represents an hydrogen atom. When they comprise a compound of formula (II), preferably no more than one of $R^1$, $R^2$ and $R^3$ represents an hydrogen atom. When they comprise a compound of formula (III), preferably no more than one of $R^4$, $R^5$ and $R^6$ represents an hydrogen atom. When they comprise a compound of formula (IV), preferably no more than one of $R^4$, $R^5$ and $R^6$ represents an hydrogen atom. When they comprise a compound of formula (V), preferably no more than one of $R^4$, $R^5$ and $R^6$ represents an hydrogen atom. When they comprise a compound of formula (VI), preferably no more than one of $R^4$, $R^5$ and $R^6$ represents an hydrogen atom. When they comprise a compound of formula (VII), preferably no more than one of $R^9$ and $R^{10}$ represents an hydrogen atom. When they comprise a compound of formula (VIII), preferably no more than one of $R^9$ and $R^{10}$ represents an hydrogen atom.

In the redox couples of scheme 1, preferably no more than one of $R^1$, $R^2$ and $R^3$ (connected to a same nitrogen atom) represents an hydrogen atom. In the redox couples of scheme 2, preferably no more than one of $R^4$, $R^5$ and $R^6$ (connected to a same phosphorus atom) represents an hydrogen atom. In the redox couples of scheme 3, preferably no more than one of $R^4$, $R^5$ and $R^6$ (connected to a same phosphorus atom) represents an hydrogen atom. In the redox couples of scheme 4, preferably no more than one of $R^9$ and $R^{10}$ (connected to a same sulphur atom) represents an hydrogen atom.

The redox couples of the present invention can be used in a solar cell, a fuel cell, a battery, a sensor or a display. They can also be used as electronic conductors in a non-polar medium.

The redox-switchable systems of the invention can be used in a solar cell, a fuel cell, a battery, a sensor or a display. They can also be used as a proton donor-acceptor to support ionic conduction in proton conducting membranes or as anti-static agents. These anti-static agents are preferably used in a non-polar medium. Such a medium is preferably petroleum or a derivative thereof, a polymer (such as polyurethanes, polyvinyl chlorides, polystyrenes, polyesters, polyethylenes, polypropylenes, or polyethylenetherephtalates), a textile, or an ink. The non-polar medium can be a non-polar solvent such as hydrocarbons, preferably alkanes, and more preferably $C_5$-$C_{15}$ alkanes.

The redox couples and the redox-switchable systems of the invention can have a $\Delta E_p$ lower than 1000 mV at 100 mV/s, preferably lower than 500 mV at 100 mV/s, more preferably lower than 300 mV at 100 mV/s, even more preferably lower than 200 mV at 100 mV/s, and still even more preferably lower than 150 mV at 100 mV/s. Alternatively, the $\Delta E_p$ can be of about 100 to about 500 mV at 100 mV/s or about 150 to about 250 mV at 100 mV/s.

The compounds, compositions, redox couples, and redox-switchable systems of the present invention can be soluble in a solvent selected from the group consisting of $CH_3CN$, $CH_2Cl_2$, EtOH, isopropanol, DMSO, amides (such as DMF), hexane, heptane, linear carbonates (such as dimethylcarbonate, diethylcarbonate, ethylmethylcarbonate), cyclic esters (such as ethylene carbonate, propylene carbonate), urea (tetramethylurea), ionic liquids such as dialkylimidazolium, trialkylsulfonium, and quaternary amine (such as $C_1$-$C_{20}$ tetraalkylammonium) and quaternary phosphonium (such as $C_1$-$C_{20}$ tetraalkylphosphonium or $C_6$-$C_{12}$ tetraarylphosphonium) salts associated with stable anion such as $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, 2.3HF, $Cl^-$, $Br^-$, $I^-$, $PF_6^-$, $BF_4^-$, $ClO_4^-$ and mixtures of these solvents. Preferably, the compounds, compositions, redox couples, and redox-switchable systems of the present invention are soluble in a solvent selected from the group consisting of $CH_3CN$, amides (such as DMF), linear carbonates (such as dimethylcarbonate, diethylcarbonate, ethylmethylcarbonate), cyclic esters (such as ethylene carbonate, propylene carbonate), ionic liquids such as dialkylimidazolium, trialkylsulfonium, and quaternary amine (such as $C_1$-$C_{20}$ tetraalkylammonium) and quaternary phosphonium (such as $C_1$-$C_{20}$ tetraalkylphosphonium or $C_6$-$C_{12}$ tetraarylphosphonium) salts associated with stable anion such as $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, 2.3HF, $Cl^-$, $Br^-$, $I^-$, $PF_6^-$, $BF_4^-$, $ClO_4^-$ and mixture of these solvents. The compounds, compositions, redox couples, and redox-switchable systems of the present invention can be in a solid form or powder form at room temperature, preferably at 25° C. They can also be liquid at room temperature, preferably at 25° C.

The redox couples and redox-switchable systems of the present invention can further comprise a supporting electrolyte (such as TBAP (tetrabutylammoniumperchlorate) $K^+TFSI^-$, $K^+FSI^-$, tetraalkylammonium with $PF_6^-$, $BF_4^-$ or $ClO_4^-$, or imidazolium with $PF_6^-$, $BF_4^-$ or $ClO_4$).

The compositions of the present invention, when dissolved into a solvent as previously defined, are preferably solutions and more preferably homogeneous solutions.

In the compounds, compositions, kits, redox couples, and redox-switchable systems of the present invention, $X^-$ is preferably $(CF_3SO_2)_2N^-$, $(FSO_2)_2N^-$, $(CF_3SO_2)_3C^-$, $CF_3SO_3^-$, $(CN)_2N^-$, $PF_6^-$, $BF_4^-$ or $ClO_4^-$. More preferably, $X^-$ is $(CF_3SO_2)_2N^-$. $(CF_3SO_2)_2N^-$ is also called TFSI or bis(trifluoromethanesulfinimide) ion.

The compositions and the redox-switchable systems are preferably in the form of uncolored and/or translucent solutions. They can have, in the visible region of the light spectrum, i.e. 400 nm to 700 nm, an absorbance of about 0.01 to about 0.50 (preferably of about 0.02 to about 0.10). In such a region of the spectrum, the composition of the present invention can have an absorption below 1.0, preferably below 0.75, more preferably below 0.50, even more preferably below 0.25, and still even more preferably below 0.1. An absorbance below 0.05 is particularly preferred and an absorbance below 0.03 is even more particularly preferred.

In accordance with a preferred embodiment of the invention, the compositions and the kits of the present invention can comprise a compound of formula (Ia) and a compound of formula (IIa):

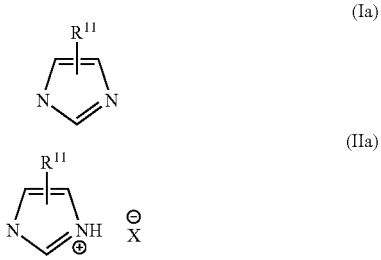

(Ia)

(IIa)

wherein $R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, $CH_2$=$CHCH_2$—, $CH_2$=$CHCH_2CH_2$—, $CH_2$=$CHC_6H_4C_pH_{2p+1}$—, $CH_2$=$CHC_pH_{2p}C_6H_4$—,

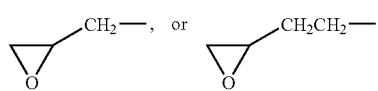

and $X^-$ is as previously defined, where n is an integer having a value from 1 to 48 (preferably 1 to 12), and p is an integer having a value from 1 to 48 (preferably 1 to 12). $R^{11}$ is preferably $CH_3$.

In accordance with another preferred embodiment of the invention, the compositions and the kits of the present invention can comprise a compound of formula (Ib) and a compound of formula (IIb):

(Ib)

(IIb)

wherein $R^{11}$ and $X^-$ are as previously defined for (Ia) and (IIa).

In accordance with another preferred embodiment of the invention, the compositions and the kits of the present invention can comprise a compound of formula (Ic) and a compound of formula (IIc):

(Ic)

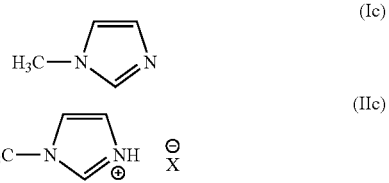

(IIc)

wherein $X^-$ is as previously defined.

In accordance with another preferred embodiment of the invention, the compositions and the kits of the present invention can comprise a compound of formula (IIIa) and a compound of formula (IVa):

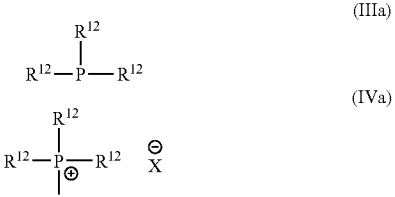

(IIIa)

(IVa)

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, (i-Pr)$_2$N—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, and $Me_3P$=N—; and $X^-$ is as previously defined, where n is an integer having a value from 1 to 48 (preferably 1 to 12).

In accordance with another preferred embodiment of the invention, the compositions and the kits of the present invention can comprise a compound of formula (IIIb) and a compound of formula (IVb):

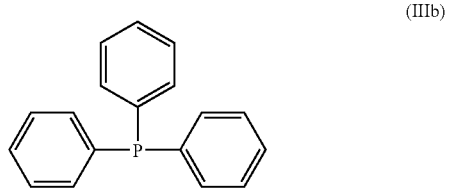

(IIIb)

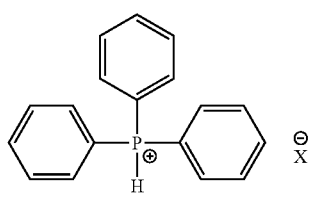
(IVb)

wherein X⁻ is as previously defined.

In accordance with another preferred embodiment of the invention, the compositions and the kits of the present invention can comprise a compound of formula (Va) and a compound of formula (VIa):

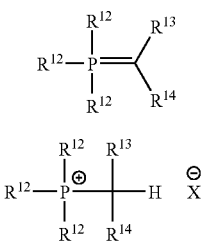
(Va)

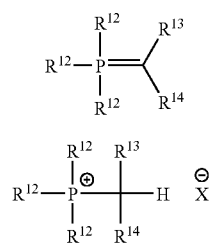
(VIa)

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $C_1$-$C_{12}$ alkyl which is linear or branched, $C_1$-$C_6$ hydroxy alkyl, $C_1$-$C_6$ alkoxy, $OC_6H_5$, and $OCH_2$—$C_6H_5$;

$R^{13}$ and $R^{14}$ are the same or different and are selected from the group consisting of a hydrogen atom, H, CN, $NO_2$, $(CH_3)_2$N—, $(C_2H_5)_2$N—, $(C_3H_7)_2$N—, $(C_4H_9)_2$N—, (i-Pr)$_2$N—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, —$SO_2H$, —$SO_2CF_3$, —$NSO_2CF_3$, —$SO_2CH_3$, and —$NSO_2CH_3$; and X⁻ is as previously defined;

where n is an integer having a value from 1 to 48 (preferably 1 to 12).

In accordance with another preferred embodiment of the invention, the compositions and the kits of the present invention can comprise a compound of formula (Vb) and a compound of formula (VIb):

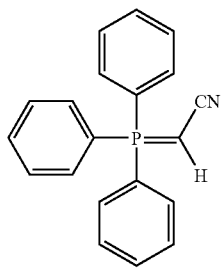
(Vb)

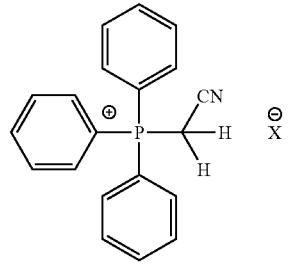
(VIb)

wherein X⁻ is as previously defined.

In accordance with another preferred embodiment of the invention, the compositions and the kits of the present invention can comprise a compound of formula (VIIa) and a compound of formula (VIIIa):

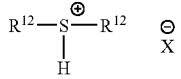
(VIIa)

(VIIIa)

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, $C_1$-$C_{12}$ alkyl which is linear or branched, a $C_1$-$C_6$ alkoxy, a $C_1$-$C_6$ hydroxy alkyl, $NO_2$, CN, $OC_6H_5$, $OCH_2$—$C_6H_5$, $CF_3$, and $C_2F_5$; and X⁻ is as previously defined.

In accordance with another preferred embodiment of the invention, the compositions and the kits of the present invention can comprise a compound of formula (VIIb) and a compound of formula (VIIIb):

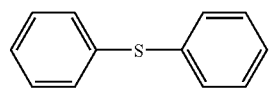
(VIIb)

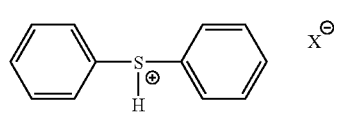
(VIIIb)

wherein X⁻ is as previously defined.

The person skilled in the art would clearly recognize that in the compositions or kits of the present invention, in the formulas as previously defined, the basic member (or base) is at the left side and the protonated member (or conjugated acid) is at the right side.

In accordance with another preferred embodiment of the invention, the redox couples can be as defined in scheme (5):

(5)

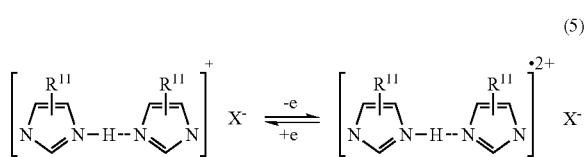

wherein $R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, $CH_2$=$CHCH_2$—, $CH_2$=$CHCH_2CH_2$—, $CH_2$=$CHC_6H_4C_pH_{2p+1}$—, $CH_2$=$CHC_pH_{2p}C_6H_4$—,

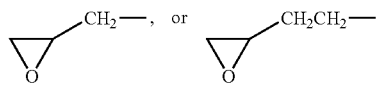

and X is as previously defined, where n is an integer having a value from 1 to 48 (preferably 1 to 12), and p is an integer having a value from 1 to 48 (preferably 1 to 12). $R^{11}$ is preferably $CH_3$.

In accordance with another preferred embodiment of the invention, the redox couple can be as defined in scheme (6):

(6)

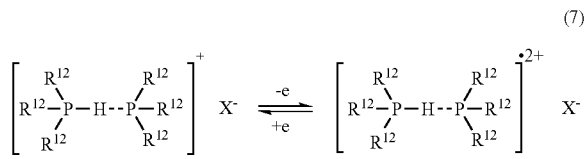

wherein $R^{11}$ and $X^-$ are as previously defined in scheme (5). $R^{11}$ is preferably $CH_3$.

In accordance with another preferred embodiment of the invention, the redox couples can be as defined in scheme (7):

(7)

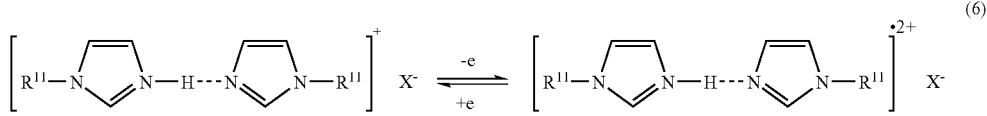

wherein $R^{12}$ is phenyl, naphtyl, pyridyl, furyl, or thiophenyl, $R^{12}$ being unsubstituted or substituted with F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, $(i$-$Pr)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, or $Me_3P$=N—; $X^-$ is as previously defined, where n is an integer having a value from 1 to 48 (preferably from 1 to 12). $R^{12}$ is preferably phenyl.

In accordance with another preferred embodiment of the invention, the redox couples can be as defined in scheme (8):

(8)

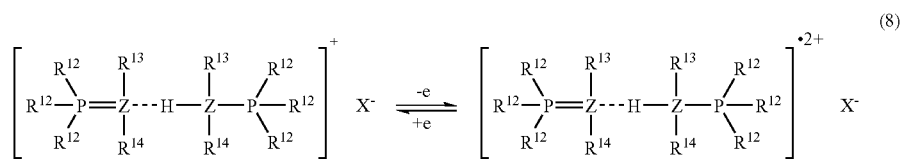

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $C_1$-$C_{12}$ alkyl which is linear or branched, $C_1$-$C_6$ hydroxy alkyl, $C_1$-$C_6$ alkoxy, $OC_6H_5$, and $OCH_2$—$C_6H_5$;

$R^{13}$ and $R^{14}$ are the same or different and are selected from the group consisting of a hydrogen atom, H, CN, $NO_2$, $(CH_3)_2N$—, $(C_2H_5)_2N$—, $(C_3H_7)_2N$—, $(C_4H_9)_2N$—, $(i$-$Pr)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, —$SO_2H$, —$SO_2CF_3$, —$NSO_2CF_3$, —$SO_2CH_3$, and —$NSO_2CH_3$; and $X^-$ is as previously defined;

where n is an integer having a value from 1 to 48 (preferably 1 to 12). Preferably, $R^{12}$ is phenyl, $R^{13}$ is CN, and $R^{14}$ is H.

In accordance with another preferred embodiment of the invention, the redox couples can be as defined in scheme (9):

(9)

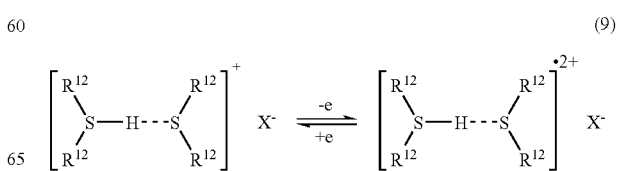

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, $C_1$-$C_{12}$ alkyl which is linear or branched, a $C_1$-$C_6$ alkoxy, a $C_1$-$C_6$ hydroxy alkyl, $NO_2$, CN, $OC_6H_5$, $OCH_2$—$C_6H_5$, $CF_3$, or $C_2F_5$, and $X^-$ is as previously defined. $R^{12}$ is preferably phenyl.

The person skilled in the art would clearly recognize that in the redox couples of the present invention, as defined in any one of the previously presented schemes, the reduced member is at the left side of the arrow and the oxidized member is at the right side of the arrow. The person skilled in the art will also understand that each of the schemes represents a family of redox couples covering several possibilities.

In accordance with another preferred embodiment of the invention, the redox-switchable systems can be as defined in scheme (14):

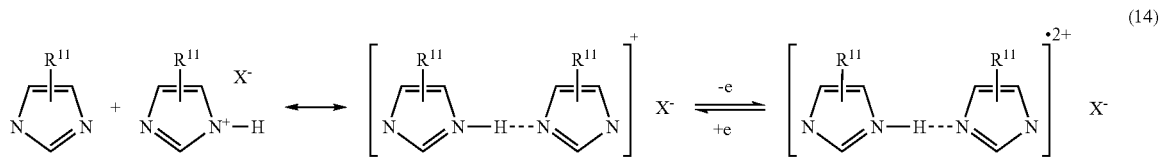

(14)

wherein $R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, $CH_2$=$CHCH_2$—, $CH_2$=$CHCH_2CH_2$—, $CH_2$=$CHC_6H_4C_pH_{2p+1}$—, $CH_2$=$CHC_pH_{2p}C_6H_4$—,

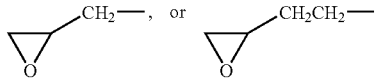

and $X^-$ is as previously defined, where n is an integer having a value from 1 to 48 (preferably from 1 to 12), and p is an integer having a value from 1 to 48 (preferably from 1 to 12). $R^{11}$ is preferably $CH_3$.

In accordance with another preferred embodiment of the invention, the redox-switchable systems can be as defined in scheme (15):

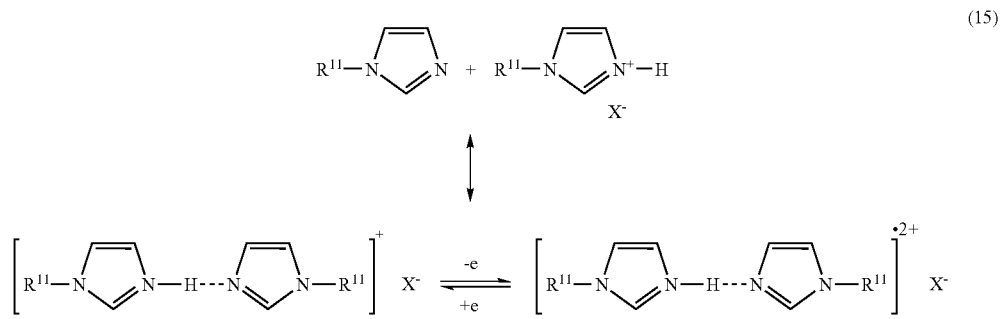

(15)

wherein $R^{11}$ and $X^-$ are as previously defined in scheme (14). $R^{11}$ is preferably $CH_3$.

In accordance with another preferred embodiment of the invention, the redox-switchable systems can be as defined in scheme (16):

alkoxy, a $C_1$-$C_6$ hydroxy alkyl, $NO_2$, CN, $C_1$-$C_{12}$ alkyl which is linear or branched, $C_1$-$C_6$ hydroxy alkyl, $C_1$-$C_6$ alkoxy, $OC_6H_5$, and $OCH_2$—$C_6H_5$;

$R^{13}$ and $R^{14}$ are the same or different and are selected from the group consisting of a hydrogen atom, H, CN, $NO_2$, $(CH_3)_2$

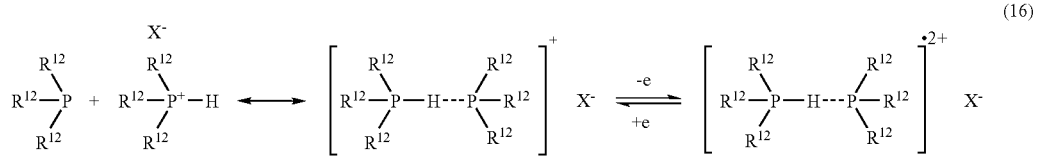

(16)

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, $(i$-$Pr)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, and $Me_3P$=N—; X is as previously defined, where n is an integer having a value from 1 to 48 (preferably 1 to 12). $R^{12}$ is preferably phenyl.

In accordance with another preferred embodiment of the invention, the redox-switchable systems can be as defined in scheme (17):

N—, $(C_2H_5)_2N$—, $(C_3H_7)_2N$—, $(C_4H_9)_2N$—, $(i$-$Pr)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, —$SO_2H$, —$SO_2CF_3$, —$NSO_2CF_3$, —$SO_2CH_3$, and —$NSO_2CH_3$; and $X^-$ is as previously defined;

where n is an integer having a value from 1 to 48 (preferably 1 to 12). Preferably, $R^{12}$ is phenyl, $R^{13}$ is CN, and $R^{14}$ is H.

In accordance with another preferred embodiment of the invention, the redox-switchable systems can be as defined in scheme (18):

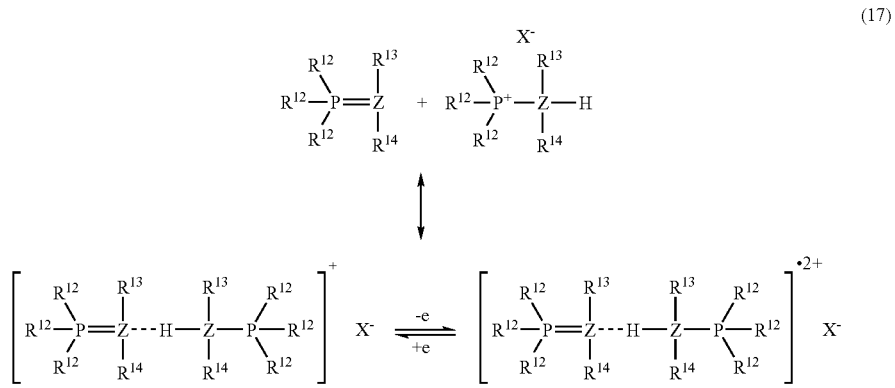

(17)

wherein
$R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$

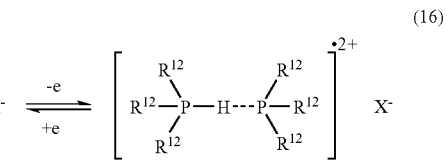

(18)

wherein $R^{12}$ is phenyl, naphtyl, pyridyl, furyl, or thiophenyl, $R^{12}$ being unsubstituted or substituted with F, Cl, Br, I, OH, $C_1$-$C_{12}$ alkyl which is linear or branched, a $C_1$-$C_6$ alkoxy, a $C_1$-$C_6$ hydroxy alkyl, $NO_2$, CN, $OC_6H_5$, $OCH_2$—$C_6H_5$, $CF_3$, or $C_2F_5$, and $X^-$ is as previously defined. $R^{12}$ is preferably phenyl.

The person skilled in the art would clearly recognize that the redox-switchable systems of the present invention can include the compositions and the redox couples of the invention. The person skilled in the art would also clearly recognize that in the redox-switchable systems of the present invention, as defined in any one of the previously presented schemes, the compounds represented in brackets "[ ]" nare redox couples as previously defined in the present invention, and that the compounds which are not in brackets represent the compounds as found in the compositions according to the present invention.

The compositions and the redox-switchable systems can further comprise a polymer (such as polyurethanes, polyvinyl chlorides, polystyrenes, polyesters, polyethylenes, polypropylenes, or polyethylenetherephtalates), a solvent (such as those previously defined in the present invention), a molten salt, an ionic liquid, a gel or a combination thereof.

According to another aspect of the invention, there is provided a photovoltaic cell comprising an anode, a cathode, and a redox couple as defined in the present invention.

According to another aspect of the invention, there is provided a photovoltaic cell comprising an anode, a cathode, and a redox-switchable system as defined in the present invention.

According to another aspect of the invention, there is provided a photovoltaic cell comprising an anode, a cathode, a redox couple as defined in the present invention, and a solvent (such as those previously defined), a polymer (such as polyethyleneoxides, polyphosphazenes, etc.), a molten salt, an ionic liquid, a gel or any combination thereof.

According to another aspect of the invention there is provided an anti-static agent comprising any one of the compositions defined in the present invention. The anti-static agent is preferably comprised within a matrix. The matrix can be a polymer (such as polyurethanes, polyvinyl chlorides, polystyrenes, polyesters, polyethylenes, polypropylenes, or polyethylenetherephtalates), a solvent (such as those previously defined in the present invention), a paper, a textile, clothes, an ink, a wax, a cleaning composition, a softening agent or composition, a petroleum-based composition, a composition comprising volatile or flammable ingredients, molded objects, shaped articles, articles comprising a polymer, electronic devices (such as a computer, TV, DVD, CD player, etc.).

According to another aspect of the invention there is provided an anti-static agent comprising a first compound selected from the group consisting of compounds of formulas (I), (III), (V), and (VII), and a second compound selected from the group consisting of compounds of formulas (II), (IV), (VI), and (VIII) wherein the compounds are as previously defined. The anti-static agent is preferably comprised within a matrix. The matrix can be a polymer (such as polyurethanes, polyvinyl chlorides, polystyrenes, polyesters, polyethylenes, polypropylenes, or polyethylenetherephtalates), a solvent (such as those previously defined in the present invention), a textile, clothes, an ink, a wax, a cleaning composition, a softening composition or agent, a petroleum-based composition, a composition comprising volatile or flammable ingredients, molded objects, shaped articles, articles comprising a polymer, electronic devices (such as a computer, TV, DVD, CD player, etc.).

The person skilled in the art will understand that, when possible, all the preferred embodiments mentioned concerning the compositions of the invention also apply to the anti-static agents of the present invention.

BRIEF DESCRIPTION OF FIGURES

Further features and advantages of the invention will become more readily apparent from the following description of preferred embodiments as illustrated by way of examples in the appended figures wherein.

DESCRIPTION OF PREFERRED EMBODIMENTS

The following non-limiting examples further illustrate the invention.

$Ph_3P/Ph_3P^+H(TFSI^-)$, $MI/MI^+H(TFSI^-)$, $Ph_3P$=CHCN/$Ph_3P^+$—$CH_2CN(TFSI^-)$ and $Ph_2S/Ph_2S^+H(TFSI^-)$ compositions (or electron activable precursors to redox couples) have been prepared according to the following general method. These compositions are indicated using the following nomenclature: basic member/protonated member.

General Procedure

The same general procedure was applied to prepare all the above mentioned compositions. 0.1 mole of the basic member ($Ph_3P$, MI, $Ph_3P$=CHCN or $Ph_2S$) was charged into a two-neck flask with magnetic stirrer. Hydrochloric acid (0.1 N) was slowly added into the flask until the total solubility of the product. Then, 30 mL of a solution of one equivalent of KTFSI in distilled water was added to the reaction mixture. A white precipitate was appearing. The corresponding target salt for each of the previously mentioned basic members, i.e. the corresponding protonated members were isolated by filtration and dried under vacuum.

The protonated members, $Ph_3P^+H(TFSI^-)$, $MI^+H(TFSI^-)$, $Ph_3P^+$—$CH_2CN(TFSI^-)$ and $Ph_2S^+H(TFSI^-)$, have been confirmed using $^{13}C$, $^1H$ and $^{31}P$-NMR.

Then, for a given composition, the basic member and the protonated member have been mixed together and dissolved into a solvent so as to obtain the aforementioned compositions. In certain tests (cyclic voltammograms), these compositions are electron-activated so as to be converted into the corresponding redox couples and redox-switchable systems. Alternatively, the compositions of the present invention can be prepared by adding, to the basic member, a quantity of an acid (HTFSI), which is less than 1 equimolar of the basic member, so as to directly obtain the desired composition.

Figure 1:
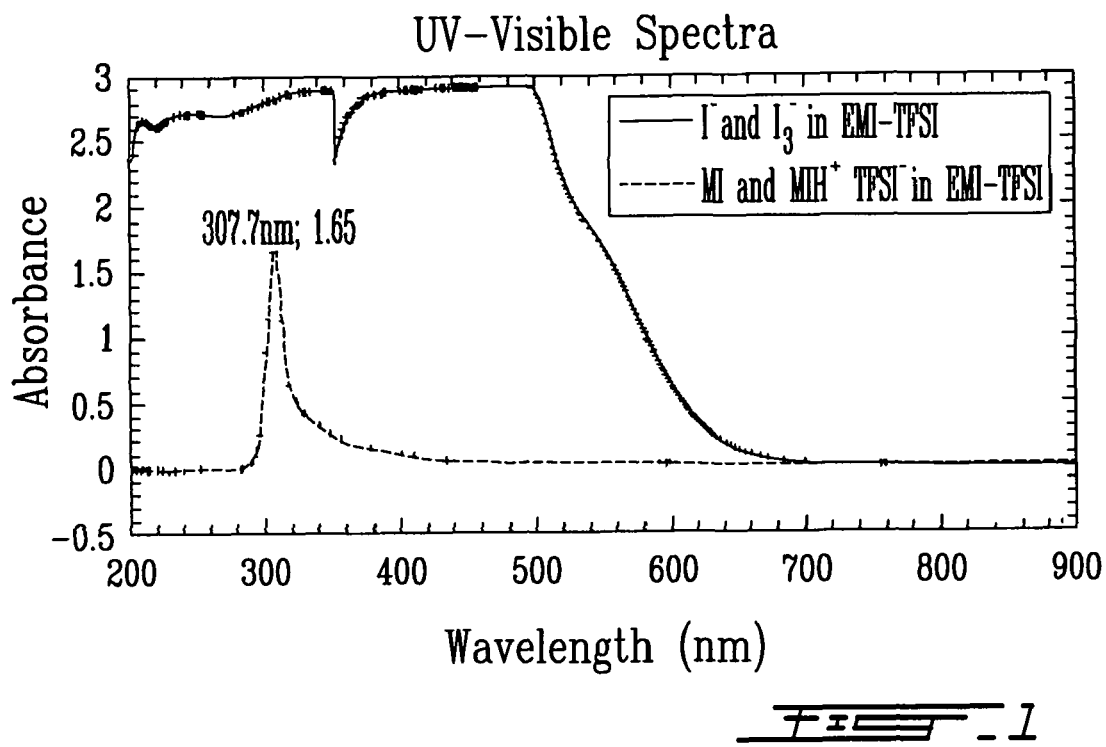
FIG. 1 shows UV-visible absorption spectra comparing a 1,3-ethylmethylimidazolium bis(trifluoromethanesulfinimide) (EMI-TFSI) solution comprising 600 mM of EMI-I and 20 mM of $I_2$, and a EMI-TFSI solution comprising 100 mM of 1-methylimidazole (MI) and 100 mM of 1-methylimidazolium-TFSI ($MI^+H$ $TFSI^-$) according to a preferred embodiment of the invention.

FIG. 1 represents UV-visible absorption spectra of a EMI-TFSI solution comprising 600 mM EMI-I and 20 mM of $I_2$ (typical of the redox electrolyte used in dye-sensitized solar cells) and of a EMI-TFSI solution comprising 100 mM of MI and 100 mM of MI$^+$H TFSI$^-$ (as prepared following the general procedure).

The absorption spectra are analyzed in Table 1, which give the absorbance of the two solutions from 300 nm (near-UV) to 700 nm as obtained using a UV-Visible spectrophotometer; the scanning speed was 150 nm/s.

TABLE 1

| Wavelength (nm) | Absorbance | |
|---|---|---|
| | $I^-/I_2$ | MI/MI$^+$H |
| 300 | 2.817 | 0.810 |
| 350 | 2.361 | 0.243 |
| 400 | 2.895 | 0.102 |
| 450 | 2.921 | 0.045 |
| 500 | 2.829 | 0.033 |
| 550 | 1.667 | 0.026 |
| 600 | 0.640 | 0.022 |
| 650 | 0.127 | 0.020 |
| 700 | 0.023 | 0.017 |

As it can be seen from FIG. 1 and Table 1, the $I^-/I_2$ composition strongly absorbs in the visible region of the light spectrum, particularly between 400 and 600 nm, whereas the MI/MI$^+$H composition does not show any significant absorption in this wavelength range. Thus, this clearly demonstrates that the MI/MI$^+$H composition would permit to considerably avoid the decrease in the energy conversion efficiency.

Figure 2:
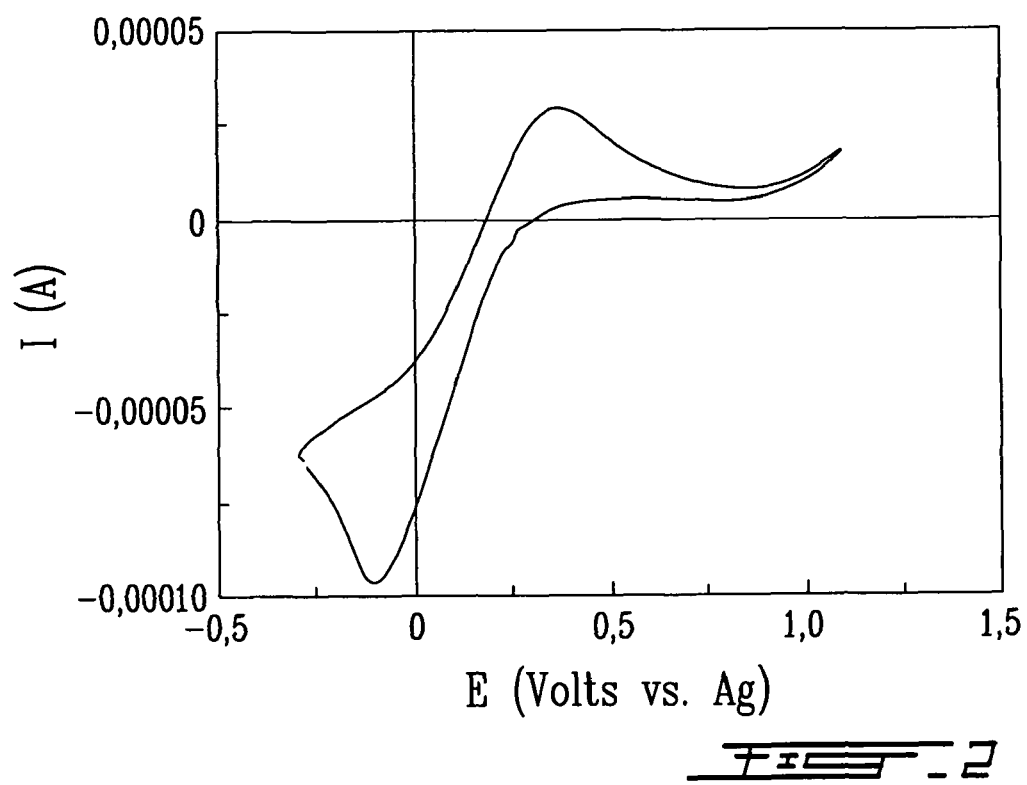
FIG. 2 shows a cyclic voltammogram at a platinum electrode of an acetonitrile solution comprising 60 mM of triphenylphosphine ($Ph_3P$), 20 mM of triphenylphosphonium-TFSI ($Ph_3P^+H$ $TFSI^-$) and 20 mM of tetrabutylammoniumperchlorate (TBAP) according to a preferred embodiment of the invention.

FIG. 2 represents a cyclic voltammogram at a platinum electrode having a surface area of 0.020 cm$^2$ with a Ag wire and a platinum electrode (0.5 cm$^2$) as the reference and counter electrode, respectively. The electrodes were immersed in an acetonitrile solution comprising 60 mM of Ph$_3$P, 20 mM of Ph$_3$P$^+$H TFSI$^-$ (as prepared following the general procedure) and 20 mM of TBAP according to a preferred embodiment of the invention. The scanning speed was 100 mV/s. As it can be seen from FIG. 2, the redox couple generated from the Ph$_3$P/Ph$_3$P$^+$H composition was tested in order to determine its electrochemical properties at a platinum electrode. The analysis shows that the redox couple obtained from the composition Ph$_3$P/Ph$_3$P$^+$H possesses a very good electrochemical behavior at this electrode. In particular, the difference between the anodic ($E_{pa}$) and cathodic ($E_{pc}$) peak potentials, symbolized as $\Delta E_p$, is 0.48 V. The redox potential is about +0.13 V.

Figure 3:
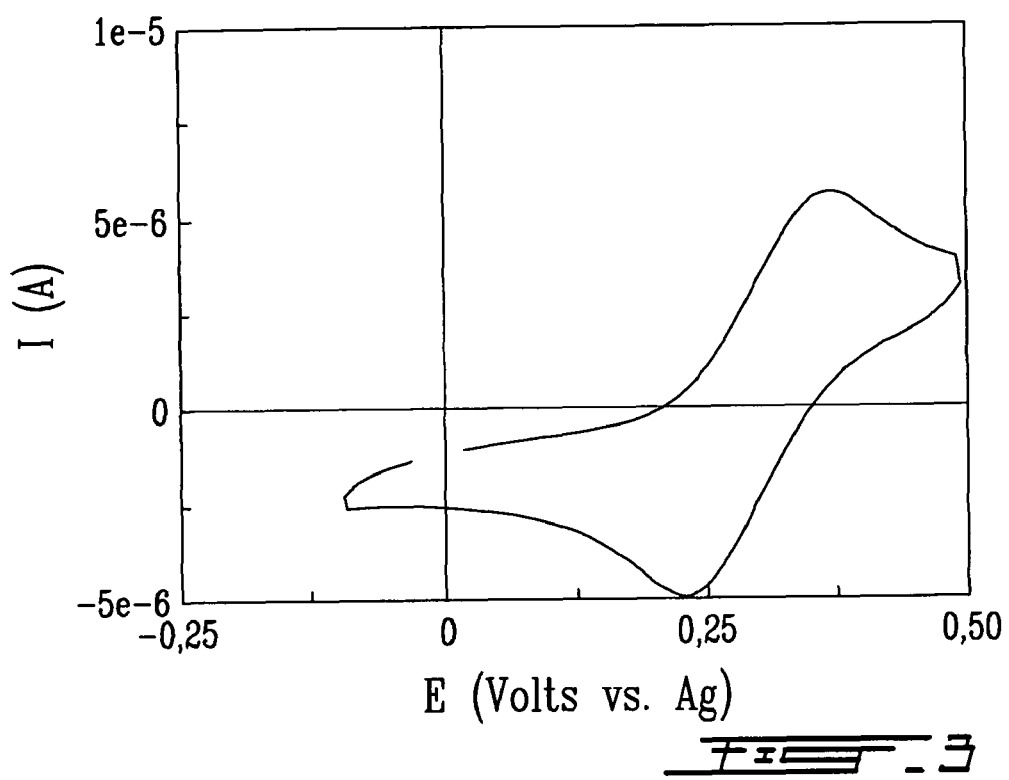
FIG. 3 shows another cyclic voltammogram at a platinum electrode of a EMI-TFSI solution comprising 28 mM of MI and 28 mM of $MI^+H$ $TFSI^-$ according to a preferred embodiment of the invention.

FIG. 3 represents a cyclic voltammogram at a platinum electrode having a surface area of 0.020 cm$^2$ with a Ag wire and a platinum electrode (0.5 cm$^2$) as the reference and counter electrode, respectively. The electrodes were immersed in a EMI-TFSI solution comprising 28 mM of MI and 28 mM of MI$^+$H TFSI$^-$ according to a preferred embodiment of the invention. The scanning speed was 100 mV/s.

As it can be seen from FIG. 3, the redox couple obtained from the MI/MI$^+$H composition was tested in order to determine its electrochemical properties at a platinum electrode. The analysis shows that such a redox couple possesses an outstanding electrochemical behavior at this electrode; in particular, the $\Delta E_p$ value is only 0.12 V. The redox potential is about +0.30 V.

Figure 4:
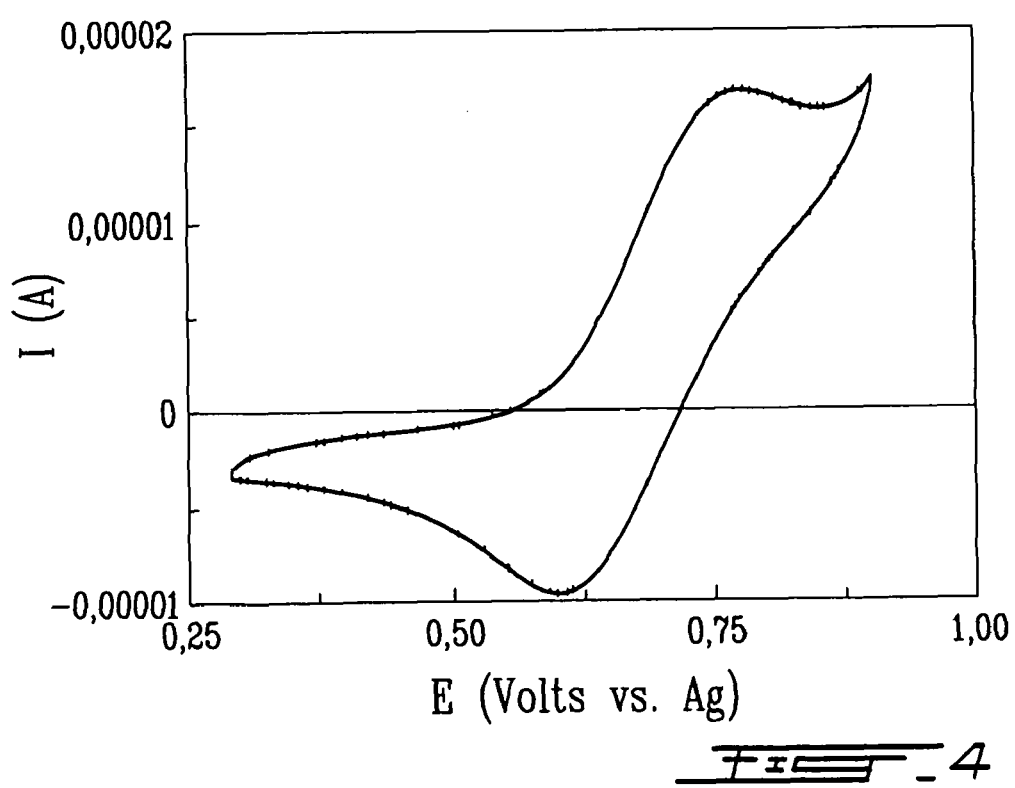
FIG. 4 shows still another cyclic voltammogram at a glassy carbon electrode of an acetonitrile solution comprising 40 mM of triphenyl(phosphranylidene)acetonitrile ($Ph_3P$=CHCN), 40 mM of triphenylphosphoniumacetonitrile-TFSI ($Ph_3P^+$—$CH_2CN$ $TFSI^-$) and 40 mM of TBAP according to a preferred embodiment of the invention.

FIG. 4 represents a cyclic voltammogram at a glassy carbon electrode having a surface area of 0.071 cm$^2$ with a Ag wire and a platinum electrode (0.5 cm$^2$) as the reference and counter electrode, respectively. The electrodes were immersed in an acetonitrile solution comprising 40 mM of Ph$_3$P=CHCN, 40 mM of Ph$_3$P$^+$—CH$_2$CN TFSI$^-$ (as prepared following the general procedure) and 40 mM of TBAP according to a preferred embodiment of the invention. The scanning speed was 100 mV/s.

As it can be seen from FIG. 4, the redox couple obtained from the Ph$_3$P=CHCN/Ph$_3$P$^+$—CH$_2$CN composition was tested in order to determine its electrochemical properties at a platinum electrode. The analysis shows that such a redox couple possesses an excellent electrochemical behavior at this electrode; in particular, the $\Delta E_p$ value is only 0.19 V. The redox potential is about +0.68 V.

Figure 5:
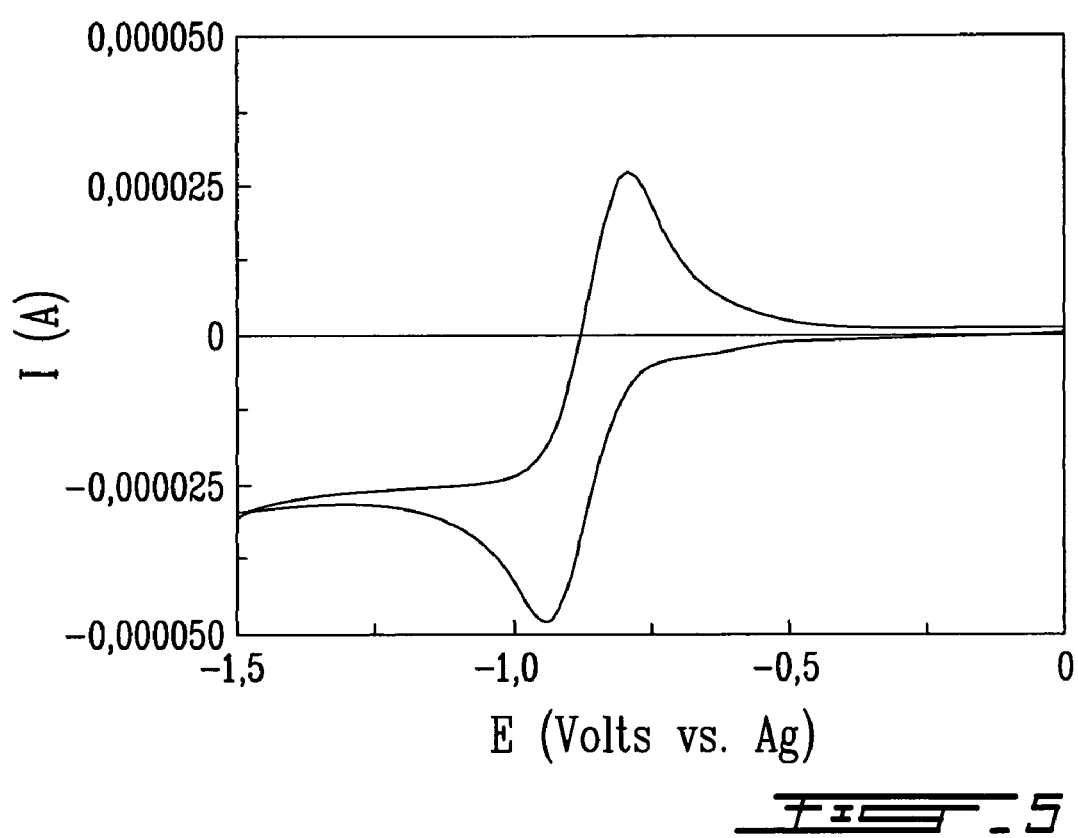
FIG. 5 shows still another cyclic voltammogram at a glassy carbon electrode of an acetonitrile solution comprising 50 mM of diphenylsulfide ($Ph_2S$), 50 mM of diphenylsulfonium-TFSI ($Ph_2S^+H$ $TFSI^-$) and 50 mM of TBAP according to a preferred embodiment of the invention.

FIG. 5 represents a cyclic voltammogram at a glassy carbon electrode having a surface area of 0.071 cm$^2$ with a Ag wire and a platinum electrode (0.5 cm$^2$) as the reference and counter electrode, respectively. The electrodes were immersed in an acetonitrile solution comprising 50 mM of Ph$_2$S, 50 mM of Ph$_2$S$^+$H TFSI$^-$ (as prepared following the general procedure) and 50 mM of TBAP according to a preferred embodiment of the invention. The scanning speed was 100 mV/s.

As it can be seen from FIG. 5, the redox couple obtained from the Ph$_2$S/Ph$_2$S$^+$H composition was tested in order to determine its electrochemical properties at a platinum electrode. The analysis shows that the redox couple possesses an outstanding electrochemical behavior at this electrode; in particular, the $\Delta E_p$ value is only 0.15 V. Moreover, the redox potential is highly electronegative with an unusual value of −0.86 V.

Table 2 gives the ionic conductivity values, at 25° C., of hexane solutions comprising trioctylphosphine (basic member) and trioctylphosphonium-TFSI (protonated member as prepared following the general procedure) at various concentrations. In these case both members of the solution have the same concentration. The measurements were carried out using a conductivity cell and electrochemical impedance spectroscopy.

TABLE 2

| | Concentration (mM) | | | | | | | |
|---|---|---|---|---|---|---|---|---|
| | 500 | 250 | 125 | 61.3 | 30.0 | 15.0 | 7.50 | 3.75 |
| Ionic conductivity (μS/cm) | 92.4 | 66.4 | 20.3 | 6.64 | 2.26 | 0.20 | 0.19 | 0.01 |

As it can be seen from Table 2, the trioctylphosphine/trioctylphosphonium composition was tested in order to determine its ionic conductivity values as a function of concentration in a non-polar solvent (hexane) to evaluate its anti-static properties. The analyses show that this composition of the two aforesaid compounds acts as an excellent anti-static agent with very high ionic conductivity values even at concentrations below 4 mM. It is noteworthy that compounds with conductivity values greater than 10$^{-3}$ μS/cm in such non-polar solvents are considered as very interesting anti-static agents. Moreover, for the utilization as anti-static agents more than one composition can be mixed together. Alternatively, the protonated member of a particular composition can be used in combination with the basic member of another composition so as to obtain different compositions (or crossed compositions), e.g. MI/Ph$_3$P$^+$H(TFSI$^-$), Ph$_3$P/ MI$^+$H(TFSI$^-$), Ph$_3$P=CHCN/Ph$_3$P$^+$H(TFSI$^-$), Ph$_3$P/Ph$_2$S$^+$ H(TFSI$^-$), MI/Ph$_2$S$^+$H(TFSI$^-$), etc.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A composition comprising a first compound selected from the group consisting of compounds of formulas (Ib), (III), (V), and (VII), and a second compound selected from the group consisting of compounds of formulas (IIb), (IV), (VI), and (VIII):

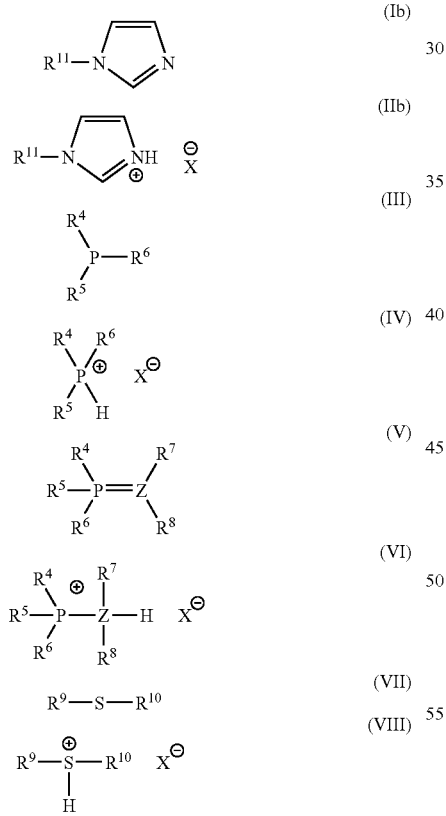

wherein

R$^4$, R$^5$ and R$^6$ are the same or different and are selected from the group consisting of a hydrogen atom, C$_1$-C$_{12}$ alkyl which is linear or branched, C$_3$-C$_{12}$ cycloalkyl, C$_1$-C$_{12}$ heterocyclyl, C$_2$-C$_8$ alkenyl, C$_2$-C$_8$ alkynyl, C$_6$-C$_{12}$ aryl, C$_6$-C$_{20}$ aralkyl, C$_6$-C$_{20}$ alkylaryl, C$_1$-C$_{12}$ heteroaryl, (CH$_3$)$_2$N—, (C$_2$H$_5$)$_2$N—, (C$_3$H$_7$)$_2$N—, (C$_4$H$_9$)$_2$N—, (i-Pr)$_2$N—, C$_n$H$_{2n+1}$, Ph$_2$P(O)—, Ph$_2$P—, Me$_2$P(O)—, Me$_2$P, Ph$_2$P(S), Me$_2$P(S), Ph$_3$P=N—, Me$_3$P=N—, and part of polymer chain or network, or R$^4$ and R$^5$ are joined together to form a 5 to 14 membered heterocyclyl in which R$^6$ is a hydrogen atom, or a bond between P and R$^4$ or between P and R$^5$; or to form a 5 to 14 membered heteroaryl ring in which R$^6$ is a hydrogen atom, a bond between P and R$^4$ or between P and R$^5$, or is a part of polymer chain or network;

R$^7$ and R$^8$ are the same or different and are selected from the group consisting of H, CF$_3$, C$_n$F$_{2n+1}$, —SO$_2$H, —SO$_2$CF$_3$, —NSO$_2$CF$_3$—, —SO$_2$CH$_3$, —NSO$_2$CH$_3$, C$_1$-C$_{12}$ alkyl which is linear or branched, C$_6$-C$_{12}$ aryl, C$_n$H$_{2n+1}$, ON, NO$_2$, Ph$_2$P (O)—, Ph$_2$P—, Me$_2$P(O)—, Me$_2$P, Ph$_2$P(S), Me$_2$P (S), Ph$_3$P=N—, Me$_3$P=N—, C$_6$H$_5$C$_p$H$_{2p}$—, C$_p$H$_{2p+1}$C$_6$H$_4$—, C$_p$H$_{2p+1}$C$_6$H$_4$C$_n$H$_{2n}$—, CH$_2$=CHC$_p$H$_{2p}$—, CH$_2$=CHC$_6$H$_5$—, CH$_2$=CHC$_6$H$_4$C$_p$H$_{2p+1}$—, CH$_2$=CHC$_p$H$_{2p}$C$_6$H$_4$—,

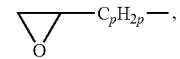

and part of polymer chain or network;

R$^9$ and R$^{10}$ are the same or different and are selected from the group consisting of a hydrogen atom, C$_1$-C$_{12}$ alkyl which is linear or branched, C$_3$-C$_{12}$ cycloalkyl, C$_1$-C$_{12}$ heterocyclyl, C$_2$-C$_8$ alkenyl, C$_2$-C$_8$ alkynyl, C$_6$-C$_{12}$ aryl, C$_6$-C$_{20}$ aralkyl, C$_6$-C$_{20}$ alkylaryl, C$_1$-C$_{12}$ heteroaryl, and part of polymer chain or network, or R$^9$ and R$^{10}$ are joined together to from a 5 to 7 membered heterocyclyl or heteroaryl;

R$^{11}$ is a C$_1$-C$_{12}$ alkyl which is linear or branched, C$_3$-C$_{12}$ cycloalkyl, C$_6$H$_5$—, C$_n$H$_{2n+1}$, C$_6$H$_5$C$_p$H$_{2p}$—, C$_p$H$_{2p+1}$C$_6$H$_4$—, C$_2$H$_{2p+1}$C$_6$H$_4$C$_n$H$_{2n}$—, CH$_2$=CHC$_p$H$_{2p}$—, CH$_2$=CHC$_6$H$_5$—, CH$_2$=CHCH$_2$—, CH$_2$=CHCH$_2$CH$_2$—, CH$_2$=CHC$_6$H$_4$C$_p$H$_{2p+1}$—, CH$_2$=CHC$_2$H$_{2p}$C$_6$H$_4$—,

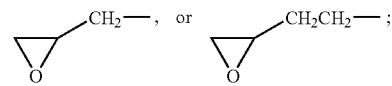

X$^-$ is (FSO$_2$)$_2$N$^-$, (CF$_3$SO$_2$)$_2$N$^-$, (C$_2$F$_5$SO$_2$)$_2$N$^-$, (CF$_3$SO$_2$)$_3$C$^-$, CF$_3$SO$_3$$^-$, CF$_3$COO$^-$, AsF$_6$$^-$, CH$_3$COO$^-$, (CN)$_2$N$^-$, NO$_3$$^-$, 2.3HF, Cl$^-$, Br$^-$, I$^-$, PF$_6$$^-$, BF$_4$$^-$, ClO$_4$$^-$, saccharin(o-benzoic sulfimide), (C$_8$H$_{16}$SO$_2$)$_2$N$^-$, or C$_3$H$_3$N$_2$$^-$; and Z is C, N or As;

said alkyl, cycloalkyl, heterocyclyl, alkenyl, alkynyl, aryl, aralkyl, alkylaryl, and heteroaryl being unsubstituted or substituted with F, Cl, Br, I, OH, a C$_1$-C$_6$ alkoxy, a C$_1$-C$_6$ hydroxy alkyl, NO$_2$, CN, CF$_3$, SO$_3$$^-$, C$_n$F$_{2n+1}$, C$_1$-C$_{12}$ alkyl which is linear or branched, C$_6$-C$_{12}$ aryl, C$_n$H$_{2n+1}$, Ph$_2$P(O)—, Ph$_2$P—, Me$_2$P (O)—, Me$_2$P, Ph$_2$P(S), Me$_2$P(S), Ph$_3$P=N—, Me$_3$P=N—, C$_6$H$_5$C$_p$H$_{2p}$—, C$_p$H$_{2p+1}$C$_6$H$_4$—, C$_p$H$_{2p+1}$C$_6$H$_4$C$_n$H$_{2n}$—, CH$_2$=CHC$_p$H$_{2p}$—, CH$_2$=CHC$_6$H$_5$—, CH$_2$=CHC$_6$H$_4$C$_p$H$_{2p+1}$—, and CH$_2$=CHC$_p$H$_{2p}$C$_6$H$_4$—, n is an integer having a value from 1 to 48 and p is an integer having a value from 1 to 48, wherein said first and second compounds of said composition are electron activated and acting as a reversible redox couple.

2. The composition of claim 1, wherein said first compound is of formula (Ib) and said second compound is of formula (IIb); said first compound is of formula (III) and said second compound is of formula (IV); said first compound is of formula (V) and said second compound is of formula (VI); or said first compound is of formula (VII) and said second compound is of formula (VIII).

3. The composition of claim 1, wherein said composition comprises a compound of formula (Ic) and a compound of formula (IIc):

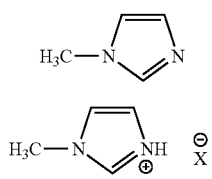

(Ic)

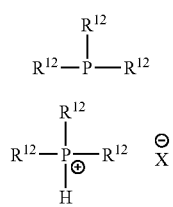

(IIc)

wherein X⁻ is as previously defined.

4. The composition of claim 1, wherein said composition comprises a compound of formula (IIIa) and a compound of formula (IVa):

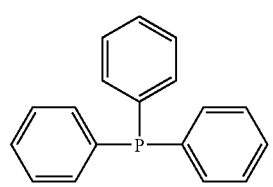

(IIIa)

(IVa)

wherein $R^{12}$ is phenyl, naphtyl, pyridyl, furyl, or thiophenyl, $R^{12}$ being unsubstituted or substituted with F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, (i-Pr)$_2$N—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, or $Me_3P$=N—; and X⁻ is as previously defined, where n is an integer having a value from 1 to 48.

5. The composition of claim 1, wherein said composition comprises a compound of formula (IIIb) and a compound of formula (IVb):

(IIIb)

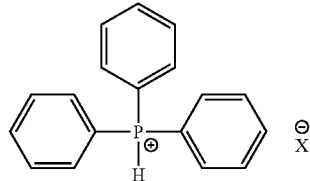

(IVb)

wherein X⁻ is as previously defined.

6. The composition of claim 1, wherein said composition comprises a compound of formula (Va) and a compound of formula (VIa):

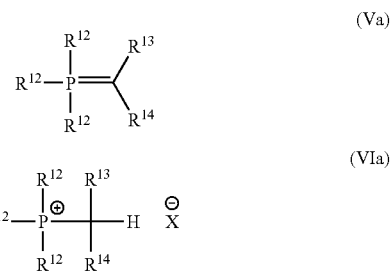

(Va)

(VIa)

wherein $R^{12}$ is phenyl, naphtyl, pyridyl, furyl, or thiophenyl, $R^{12}$ being unsubstituted or substituted with F, Cl, Br, I, OH, a $C_1$-$C_6$ alkoxy, a $C_1$-$C_6$ hydroxy alkyl, $NO_2$, CN, $C_1$-$C_{12}$ alkyl which is linear or branched, $C_1$-$C_6$ hydroxy alkyl, $C_1$-$C_6$ alkoxy, $OC_6H_5$, or $OCH_2$—$C_6H_5$;

$R^{13}$ and $R^{14}$ are the same or different and are selected from the group consisting of a hydrogen atom, H, CN, $NO_2$, $(CH_3)_2N$—, $(C_2H_5)_2N$—, $(C_3H_7)_2N$—, $(C_4H_9)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, —$SO_2H$, —$SO_2CF_3$, —$NSO_2CF_3$, —$SO_2CH_3$, —$NSO_2CH_3$, and $PO_3^{2-}$; and X⁻ is as previously defined;

where n is an integer having a value from 1 to 48.

7. The composition of claim 1, wherein said composition comprises a compound of formula (Vb) and a compound of formula (VIb):

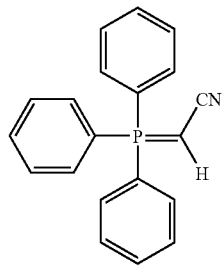

(Vb)

-continued (VIb)

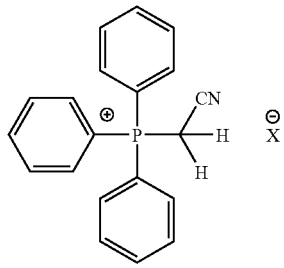

wherein X⁻ is as previously defined.

8. The composition of claim 1, wherein said composition comprises a compound of formula (VIIa) and a compound of formula (VIIIa):

(VIIa)

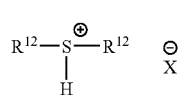
(VIIIa)

wherein $R^{12}$ is phenyl, naphtyl, pyridyl, furyl, or thiophenyl, $R^{12}$ being unsubstituted or substituted with F, Cl, Br, I, OH, $C_1$-$C_{12}$ alkyl which is linear or branched, a $C_1$-$C_6$ alkoxy, a $C_1$-$C_6$ hydroxy alkyl, $NO_2$, CN, $OC_6H_5$, $OCH_2$—$C_6H_5$, $CF_3$, or $C_2F_5$; and X⁻ is as previously defined.

9. The composition of claim 1, wherein said composition comprises a compound of formula (VIIb) and a compound of formula (VIIIb):

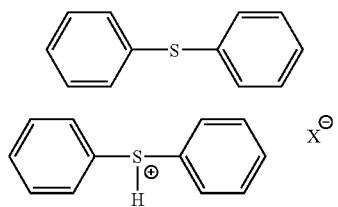
(VIIb)

(VIIIb)

wherein X⁻ is as previously defined.

10. The composition of claim 1, wherein X⁻ is $(CF_3SO_2)_2N^-$, $(FSO_2)_2N^-$, $(CF_3SO_2)_3C^-$, $CF_3SO_3^-$, $(CN)_2N^-$, $PF_6^-$, $BF_4^-$ or $ClO_4^-$.

11. The composition of claim 1, wherein X⁻ is $(CF_3SO_2)_2N^-$.

12. The composition of claim 1, wherein said composition has an absorbance of about 0.01 to about 0.50 in the visible region of the light spectrum.

13. The composition of claim 1, wherein said composition has a conductivity of at least $10^{-7}$ S/cm at 25° C. at a 1 mM concentration for each of said first and second compounds.

14. The composition of claim 1, further comprising a solvent, a polymer, a molten salt, an ionic liquid, a gel or a combination thereof.

15. An anti-static agent comprising a composition comprising a first compound selected from the group consisting of compounds of formulas (Ib), (III), (V), and (VII), and a second compound selected from the group consisting of compounds of formulas (IIb), (IV), (VI), and (VIII):

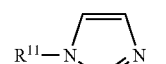
(Ib)

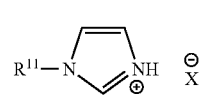
(IIb)

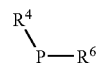
(III)

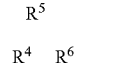
(IV)

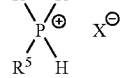
(V)

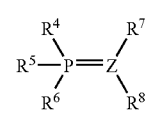
(VI)

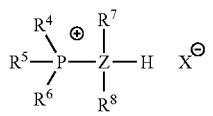
(VII)

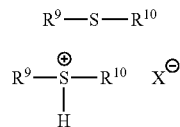
(VIII)

wherein $R^4$, $R^5$ and $R^6$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, $(CH_3)_2N$—, $(C_2H_5)_2N$—, $(C_3H_7)_2N$—, $(C_4H_9)_2N$—, $(i\text{-}Pr)_2N$—, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, and part of polymer chain or network, or $R^4$ and $R^5$ are joined together to form a 5 to 14 membered heterocyclyl in which $R^6$ is a hydrogen atom, or a bond between P and $R^4$ or between P and $R^5$; or to form a 5 to 14 membered heteroaryl ring in which $R^6$ is a hydrogen atom, a bond between P and $R^4$ or between P and $R^5$, or is a part of polymer chain or network;

$R^7$ and $R^8$ are the same or different and are selected from the group consisting of H, $CF_3$, $C_nF_{2n+1}$, —$SO_2H$, —$SO_2CF_3$, —$NSO_2CF_3$—, —$SO_2CH_3$, —$NSO_2CH_3$, $C_1$-$C_{12}$ alkyl which is linear or branched, $C_6$-$C_{12}$ aryl, $C_nH_{2n+1}$, CN, $NO_2$, $Ph_2P(O)$—, $Ph_2P$—, $Me_2P(O)$—, $Me_2P$, $Ph_2P(S)$, $Me_2P(S)$, $Ph_3P$=N—, $Me_3P$=N—, $C_6H_6C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, $CH_2$=$CHC_6H_4C_pH_{2p+1}$—, $CH_2$=$CHC_pH_{2p}C_6H_4$—,

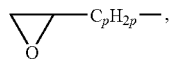

and part of polymer chain or network;

$R^9$ and $R^{10}$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^9$ and $R^{10}$ are joined together to from a 5 to 7 membered heterocyclyl or heteroaryl;

$R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, (O)—, $Me_2P$, $Ph_2P(S)$, $Me_2P(S)$, $Ph_3P$=$N$—, $Me_3P$=$N$—, $C_6H_5C_pH_{2p}$—, $C_pH_{2p+1}C_6H_4$—, $C_pH_{2p+1}C_6H_4C_nH_{2n}$—, $CH_2$=$CHC_pH_{2p}$—, $CH_2$=$CHC_6H_5$—, $CH_2$=$CHC_6H_4C_pH_{2p+1}$—, and $CH_2$=$CHC_pH_{2p}C_6H_4$—, n is an integer having a value from 1 to 48 and p is an integer having a value from 1 to 48, wherein said first and second compounds of said composition are electron activated and acting as a redox couple.

16. The anti-static agent of claim 15, wherein said first compound is of formula (Ib) and said second compound is of formula (IIb); said first compound is of formula (III) and said second compound is of formula (IV); said first compound is of formula (V) and said second compound is of formula (VI); or said first compound is of formula (VII) and said second compound is of formula (VIII).

17. A redox couple according to any one of schemes 2 to 4 and 6:

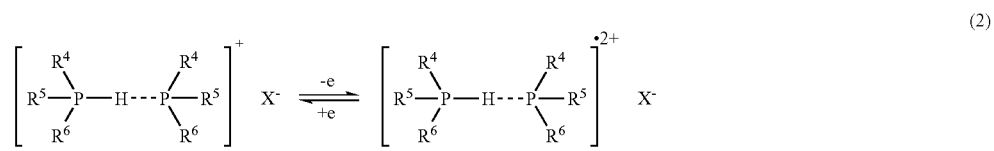 (2)

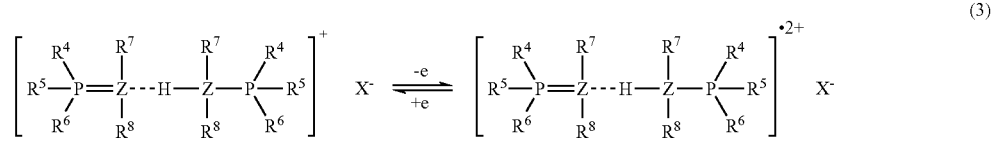 (3)

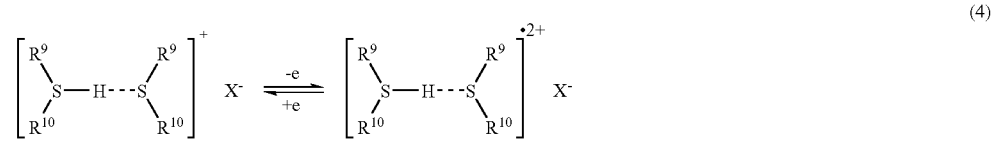 (4)

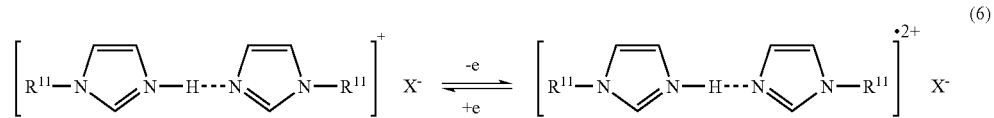 (6)

$CH_2$=$CHCH_2$—, $CH_2$=$CHCH_2CH_2$—, $CH_2$=$CHC_6H_4C_pH_{2p+1}$—, $CH_2$=$CHC_pH_{2p}C_6H_4$—,

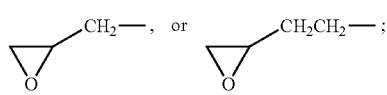

$X^-$ is $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, 2.3HF, $Cl^-$, $Br^-$, $I^-$, $PF_6^-$, $BF_4^-$, $ClO_4^-$, saccharin(o-benzoic sulfimide), $(C_8H_{16}SO_2)_2N^-$, or $C_3H_3N_2^-$; and Z is C, N or As;

said alkyl, cycloalkyl, heterocyclyl, alkenyl, alkynyl, aryl, aralkyl, alkylaryl, and heteroaryl being unsubstituted or substituted with F, Cl, Br, I, OH, a $C_1$-$C_6$ alkoxy, a $C_1$-$C_6$ hydroxy alkyl, $NO_2$, CN, $CF_3$, $SO_3^-$, $C_nF_{2n+1}$, $C_1$-$C_{12}$ alkyl which is linear or branched, $C_6$-$C_{12}$ aryl, $C_nH_{2n+1}$, $Ph_2P(O)$—, $Ph_2P$—, $Me_2P$ wherein $R^4$, $R^5$ and $R^6$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, $(CH_3)_2N$—, $(C_2H_5)_2N$—, $(C_3H_7)_2N$—, $(C_4H_9)_2N$—, $(i-Pr)_2N$—, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=$N$—, $Me_3P$=$N$—, and part of polymer chain or network, or $R^4$ and $R^5$ are joined together to form a 5 to 14 membered heterocyclyl in which $R^6$ is a hydrogen atom, or a bond between P and $R^4$ or between P and $R^5$; or to form a 5 to 14 membered heteroaryl ring in which $R^6$ is a hydrogen atom, a bond between P and $R^4$ or between P and $R^5$, or is a part of polymer chain or network;

$R^7$ and $R^8$ are the same or different and are selected from the group consisting of H, $CF_3$, $C_nF_{2n+1}$, —$SO_2H$, —$SO_2CF_3$, —$NSO_2CF_3$—, —$SO_2CH_3$, —$NSO_2CH_3$, $C_1$-$C_{12}$ alkyl which is linear or branched, $C_6$-$C_{12}$ aryl, $C_nH_{2n+1}$, CN, $NO_2$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4C_nH_{2n}$—, $CH_2=CHC_pH_{2p}$—, $CH_2=CHC_6H_5$—, $CH_2=CHC_6H_4C_pH_{2p+1}$—, $CH_2=CHC_pH_{2p}C_6H_4$—,

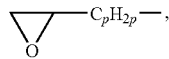

and part of polymer chain or network;

$R^9$ and $R^{10}$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^9$ and $R^{10}$ are joined together to from a 5 to 7 membered heterocyclyl or heteroaryl;

$R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHCH_2$—, $CH_2=CHCH_2CH_2$—, $CH_2=CHC_6H_4C_pH_{2p+1}$—, $CH_2=CHC_pH_{2p}C_6H_4$—,

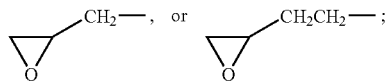

$X^-$ is $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, 2.3HF, $Cl^-$, $Br^-$, $I^-$, $PF_6^-$, $BF_4^-$, $ClO_4^-$, saccharin(o-benzoic sulfimide), $(C_8H_{16}SO_2)_2N^-$, or $C_3H_3N_2^-$; and Z is C, N or As;

said alkyl, cycloalkyl, heterocyclyl, alkenyl, alkynyl, aryl, aralkyl, alkylaryl, and heteroaryl being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $CF_3$, $SO_3$, $C_nF_{2n+1}$, $C_1$-$C_{12}$ alkyl which is linear or branched, $C_6$-$C_{12}$ aryl, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHC_6H_4C_pH_{2p+1}$—, and $CH_2=CHC_pH_{2p}C_6H_4$—, where n is an integer having a value from 1 to 48 and p is an integer having a value from 1 to 48.

18. The redox couple of claim 17, wherein said redox couple is as defined in scheme (7):

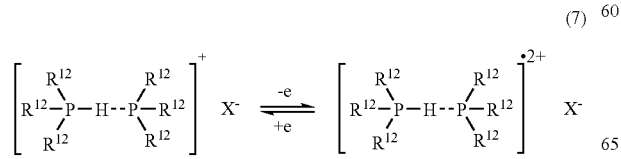

(7)

wherein $R^{12}$ is phenyl, naphtyl, pyridyl, furyl, or thiophenyl, $R^{12}$ being unsubstituted or substituted with 1 to 3 substituents selected from the group consisting of F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, (i-Pr)$_2$N—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, and $Me_3P=N$—;

$X^-$ is as previously defined, where n is an integer having a value from 1 to 48.

19. The redox couple of claim 17, wherein said redox couple has a $\Delta E_p$ lower than 200 mV at 100 mV/s.

20. The redox couple of claim 17, wherein said redox couple has a $\Delta E_p$ lower than 500 mV at 100 mV/s.

21. A composition comprising a first compound selected from the group consisting of compounds of formulas (Ib), (III), (V), and (VII), and a second compound selected from the group consisting of compounds of formulas (IIb), (IV), (VI), and (VIII):

(Ib)

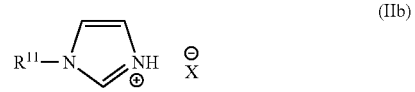
(IIb)

(III)

(IV)

(V)

(VI)

(VII)

(VIII)

wherein $R^4$, $R^5$ and $R^6$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, $(CH_3)_2N$—, $(C_2H_5)_2N$—, $(C_3H_7)_2N$—, $(C_4H_9)_2N$—, (i-Pr)$_2$N—, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, and part of polymer chain or network, or $R^4$ and $R^5$ are joined together to form a 5 to 14 membered heterocyclyl in which $R^6$ is a hydrogen atom, or a bond between P and $R^4$ or between P and $R^5$; or to form a 5 to 14 membered heteroaryl ring in which $R^6$ is a hydrogen atom, a bond between P and $R^4$ or between P and $R^5$, or is a part of polymer chain or network;

$R^7$ and $R^8$ are the same or different and are selected from the group consisting of H, $CF_3$, $C_nF_{2n+1}$, —$SO_2H$, —$SO_2CF_3$, —$NSO_2CF_3$—, —$SO_2CH_3$, —$NSO_2CH_3$, $C_1$-$C_{12}$ alkyl which is linear or branched, $C_6$-$C_{12}$ aryl, $C_nH_{2n+1}$, ON, $NO_2$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHC_6H_4C_pH_{2p+1}$—, $CH_2=CHC_pH_{2p}C_6H_4$—,

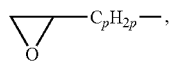

and part of polymer chain or network;

$R^9$ and $R^{10}$ are the same or different and are selected from the group consisting of a hydrogen atom, $C_1$-$C_{12}$ alkyl which is linear or branched, $C_3$-$C_{12}$ cycloalkyl, $C_1$-$C_{12}$ heterocyclyl, $C_2$-$C_8$ alkenyl, $C_2$-$C_8$ alkynyl, $C_6$-$C_{12}$ aryl, $C_6$-$C_{20}$ aralkyl, $C_6$-$C_{20}$ alkylaryl, $C_1$-$C_{12}$ heteroaryl, and part of polymer chain or network, or $R^9$ and $R^{10}$ are joined together to from a 5 to 7 membered heterocyclyl or heteroaryl; and $R^{11}$ is a $C_1$-$C_{12}$ alkyl which is linear or branched, $C_3$-$C_{12}$ cycloalkyl, $C_6H_5$—, $C_nH_{2n+1}$, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHCH_2$—, $CH_2=CHCH_2CH_2$—, $CH_2=CHC_6H_4C_pH_{2p+1}$—, $CH_2=CHC_pH_{2p}C_6H_4$—,

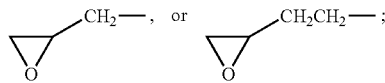

$X^-$ is $(FSO_2)_2N^-$, $(CF_3SO_2)_2N^-$ or $(C_2F_5SO_2)_2N^-$; and Z is C, N or As;

said alkyl, cycloalkyl, heterocyclyl, alkenyl, alkynyl, aryl, aralkyl, alkylaryl, and heteroaryl being unsubstituted or substituted with F, Cl, Br, I, OH, a $C_1$-$C_6$ alkoxy, a $C_1$-$C_6$ hydroxy alkyl, $NO_2$, CN, $CF_3$, $SO_3^-$, $C_nF_{2n+1}$, $C_1$-$C_{12}$ alkyl which is linear or branched, $C_6$-$C_{12}$ aryl, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, $C_6H_5C_pH_{2p}$—, $C_pH_{2p+1}C_6H_4$—, $C_pH_{2p+1}C_6H_4C_nH_{2n}$—, $CH_2=CHC_pH_{2p}$—, $CH_2=CHC_6H_5$—, $CH_2=CHC_6H_4C_pH_{2p+1}$—, and $CH_2=CHC_pH_{2p}C_6H_4$—, n is an integer having a value from 1 to 48 and p is an integer having a value from 1 to 48, wherein said first and second compounds of said composition are electron activated and acting as a redox couple.

22. The composition of claim 5, wherein $X^-$ is $(CF_3SO_2)_2N^-$, $(FSO_2)_2N^-$, or $(C_2F_6SO_2)_2N^-$.

23. The composition of claim 5, wherein $X^-$ is $(CF_3SO_2)_2N^-$.

24. The composition of claim 21, wherein said first compound is of formula (Ib) and said second compound is of formula (IIb); said first compound is of formula (III) and said second compound is of formula (IV); said first compound is of formula (V) and said second compound is of formula (VI); or said first compound is of formula (VII) and said second compound is of formula (VIII).

25. The composition of claim 21, wherein said composition comprises a compound of formula (III) and a compound of formula (IV) and wherein $R^4$, $R^5$ and $R^6$ are the same and each represents an unsubstituted $C_6$-$C_{12}$ aryl.

26. The composition of claim 1, wherein $R^{11}$ is a $C_1$-$C_{12}$ alkyl, and $X^-$ is $(CF_3SO_2)_2N^-$, $(FSO_2)_2N^-$, or $(C_2F_5SO_2)_2N^-$.

27. The composition of claim 1, wherein said redox couple has a $\Delta E_p$ lower than 500 mV at 100 mV/s.

28. The composition of claim 1, wherein said redox couple has a $\Delta E_p$ lower than 200 mV at 100 mV/s.

29. The redox couple of claim 18, wherein $R^{12}$ is an unsubstituted phenyl and $X^-$ is $(CF_3SO_2)_2N^-$, $(FSO_2)_2N^-$, or $(C_2F_5SO_2)_2N^-$.

30. The redox couple of claim 29, wherein $X^-$ is $(CF_3SO_2)_2N^-$.

31. The composition of claim 9, wherein $X^-$ is $(CF_3SO_2)_2N^-$.

32. The composition of claim 26, wherein $X^-$ is $(CF_3SO_2)_2N^-$.

33. The composition of claim 21, wherein said first compound is of formula (Va) and said second compound is of formula (VIa):

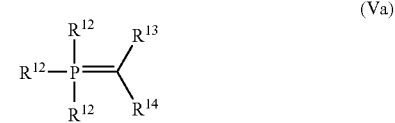

(Va)

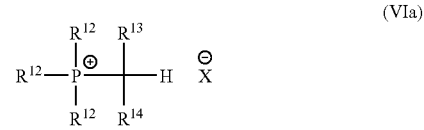

(VIa)

wherein $R^{12}$ is phenyl, naphtyl, pyridyl, furyl, or thiophenyl, $R^{12}$ being unsubstituted or substituted with F, Cl, Br, I, OH, a $C_1$-$C_6$ alkoxy, a $C_1$-$C_6$ hydroxy alkyl, $NO_2$, CN, $C_1$-$C_{12}$ alkyl which is linear or branched, $C_1$-$C_6$ hydroxy alkyl, $C_1$-$C_6$ alkoxy, $OC_6H_5$, or $OCH_2$—$C_6H_5$;

$R^{13}$ and $R^{14}$ are the same or different and are selected from the group consisting of a hydrogen atom, H, CN, $NO_2$, $(CH_3)_2N$—, $(C_2H_5)_2N$—, $(C_3H_7)_2N$—, $(C_4H_9)_2N$—, $(i-Pr)_2N$—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P=N$—, $Me_3P=N$—, —$SO_2H$, —$SO_2CF_3$, —$NSO_2CF_3$, —$SO_2CH_3$, —$NSO_2CH_3$, and $PO_3^{2-}$; and $X^-$ is as previously defined;

where n is an integer having a value from 1 to 48.

34. The composition of claim 21, wherein said first compound is of formula (Vb) and said second compound is of formula (VIb):

(Vb)

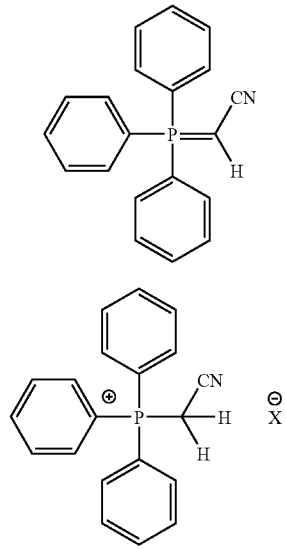

(VIb)

wherein X⁻ is as previously defined.

35. The composition of claim 21, wherein said first compound is of formula (VIIa) and said second compound is of formula (VIIIa):

$$R^{12}-S-R^{12}$$ (VIIa)

$$R^{12}-\overset{\oplus}{\underset{H}{S}}-R^{12} \quad \overset{\ominus}{X}$$ (VIIIa)

wherein $R^{12}$ is phenyl, naphtyl, pyridyl, furyl, or thiophenyl, $R^{12}$ being unsubstituted or substituted with F, Cl, Br, I, OH, $C_1$-$C_{12}$ alkyl which is linear or branched, a $C_1$-$C_6$ alkoxy, a $C_1$-$C_6$ hydroxy alkyl, $NO_2$, CN, $OC_6H_5$, $OCH_2$—$C_6H_5$, $CF_3$, or $C_2F_5$; and X⁻ is as previously defined.

36. The composition of claim 21, wherein said first compound is of formula (VIIb) and said second compound is of formula (VIIIb):

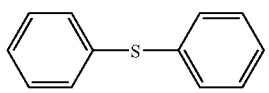
(VIIb)

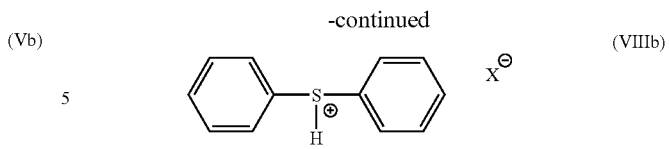
(VIIIb)

wherein X⁻ is as previously defined.

37. The composition of claim 33, wherein X⁻ is $(CF_3SO_2)_2N^-$.

38. The composition of claim 35, wherein X⁻ is $(CF_3SO_2)_2N^-$.

39. The composition of claim 1, wherein said first compound is of formula (IIIa) and said second compound is of formula (IVa):

$$R^{12}-\underset{\underset{R^{12}}{|}}{P}-R^{12}$$ (IIIa)

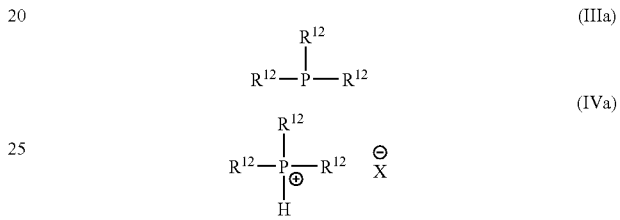
(IVa)

wherein $R^{12}$ is phenyl, naphtyl, pyridyl, furyl, or thiophenyl, $R^{12}$ being unsubstituted or substituted with F, Cl, Br, I, OH, a $C_1$-$C_6$ alkoxy, a $C_1$-$C_6$ hydroxy alkyl, $NO_2$, CN, $(CH_3)_2N$—, $(C_2H_5)_2N$—, $(C_3H_7)_2N$—, $(C_4H_9)_2N$—, (i-Pr)$_2$N—, $C_1$-$C_{12}$ alkyl which is linear or branched, $C_nH_{2n+1}$, $Ph_2P(O)$—, $Ph_2P$—, $Me_2P(O)$—, $Me_2P$, $Ph_2P(S)$, $Me_2P(S)$, $Ph_3P$=N—, or $Me_3P$=N—; and X is $(FSO_2)_2N^-$, $(CF_3SO_2)_2N$ or $(C_2F_5SO_2)_2N^-$;

where n is an integer having a value from 1 to 48.

40. The composition of claim 1, wherein said first compound is of formula (III) and said second compound is of formula (IV); said first compound is of formula (V) and said second compound is of formula (VI); or said first compound is of formula (VII) and said second compound is of formula (VIII).

41. The composition of claim 21, wherein said first compound is of formula (III) and said second compound is of formula (IV); said first compound is of formula (V) and said second compound is of formula (VI); or said first compound is of formula (VII) and said second compound is of formula (VIII).

* * * * *

UNITED STATES PATENT AND TRADEMARK OFFICE
CERTIFICATE OF CORRECTION

PATENT NO. : 7,851,091 B2
APPLICATION NO. : 11/299967
DATED : December 14, 2010
INVENTOR(S) : Amer Hammami and Benoit Marsan It is certified that error appears in the above-identified patent and that said Letters Patent is hereby corrected as shown below:

In column 28, line 15, the term "ON" should read -- CN --;
In column 28, line 39, the term "C2H2p+1C6H4CnH2n–" should read -- CpH2p+1C6H4CnH2n– --;
In column 28, line 43, the term "CH2=CHC2H2pC6H4–" should read -- CH2=CHCpH2pC6H4– --;
In column 30, line 43, the term -- (i-Pr)2N– -- should be inserted between "(C4H9)2N–" and "C1-C12 alkyl";
In column 31, line 60, the term "25° C." should read -- 25°C --;
In column 32, line 63, the "C6H6CpH2p–" should read -- C6H5CpH2p– --;
In column 33, line 14, the word "from" should read -- form --;
In column 33, line 47, the term "CH2=CHC6H4C2H2p+1–" should read -- CH2=CHC6H4CpH2p+1– --;
In column 35, line 4, the term -- CpH2p+1C6H4– -- should be inserted between the terms "C6H5CpH2p–" and "CpH2p+1C6H4CnH2n–";
In column 35, line 21, the word "from" should read -- form --;
In column 37, line 10, the term "ON" should read -- CN --;
In column 37, line 30, the word "from" should read -- form --;
In column 37, line 31, the word "and" should be deleted;
In column 37, line 62, the term "(C2F6SO2)2N-" should read -- (C2F5SO2)2N- --; and
In column 40, line 37, the term "X is (FSO2)2N-, (CF3SO2)2N" should read -- X- is (FSO2)2N-, (CF3SO2)2N- --.

Signed and Sealed this
Twenty-seventh Day of September, 2011

David J. Kappos
*Director of the United States Patent and Trademark Office*